US011434463B2

(12) United States Patent
Armani et al.

(10) Patent No.: US 11,434,463 B2
(45) Date of Patent: Sep. 6, 2022

(54) SYSTEMS, APPARATUS AND METHODS FOR CONTROLLING A MOVEMENT OF A CELL CULTURE TO OPTIMIZE CELL GROWTH

(71) Applicant: VBC Holdings LLC, Culver (IT)

(72) Inventors: Francesco Armani, Udine (IT); Giacomo Cattaruzzi, Fagagna (IT); Francesco Curcio, Pagnacco (IT); Massimo Moretti, Povoletto (IT); Antonio Sfiligoj, Duino Aurisina (IT); Piero Fissore, Udine (IT)

(73) Assignee: VBC Holdings LLC, Culver City, CA (US)

( * ) Notice: Subject to any disclaimer, the term of this patent is extended or adjusted under 35 U.S.C. 154(b) by 109 days.

(21) Appl. No.: 17/007,957

(22) Filed: Aug. 31, 2020

(65) Prior Publication Data

US 2020/0399580 A1    Dec. 24, 2020

Related U.S. Application Data

(63) Continuation of application No. 15/703,500, filed on Sep. 13, 2017, now Pat. No. 10,801,005.
(Continued)

(51) Int. Cl.
*C12M 1/34* (2006.01)
*C12M 1/36* (2006.01)
(Continued)

(52) U.S. Cl.
CPC ............ *C12M 41/36* (2013.01); *C12M 23/04* (2013.01); *C12M 27/16* (2013.01); *C12M 41/48* (2013.01);
(Continued)

(58) Field of Classification Search
None
See application file for complete search history.

(56) References Cited

U.S. PATENT DOCUMENTS 6,544,788 B2    4/2003  Singh
8,481,305 B2    7/2013  Kim et al.
(Continued)

FOREIGN PATENT DOCUMENTS

EP    2995676    3/2016
JP    H03-7575   1/1991
(Continued)

OTHER PUBLICATIONS

International Search Report and Written Opinion for the corresponding PCT/US2017/051350 filed Sep. 13, 2017 dated Dec. 20, 2017 (24 pages).
(Continued)

*Primary Examiner* — Santiago Garcia
(74) *Attorney, Agent, or Firm* — Lucas & Mercanti, LLP

(57) ABSTRACT

A system for controlling a motion of a cell culture includes a tray adapted to hold a cell culture, a camera adapted to capture an image of the cell culture, and a device adapted to control a movement of the tray. The system also includes a processor adapted to determine a first movement of the tray, receive from the camera data representing an image of the cell culture, determine a characteristic of the cell culture based on the image data, determine a second movement of the tray based on the characteristic, the second movement being different from the first movement, and cause the tray to move in accordance with the second movement.

19 Claims, 25 Drawing Sheets

Related U.S. Application Data

(60) Provisional application No. 62/394,569, filed on Sep. 14, 2016.

(51) Int. Cl.

| | | |
|---|---|---|
| *G06V 20/69* | (2022.01) | |
| *C12M 1/12* | (2006.01) | |
| *C12M 3/06* | (2006.01) | |
| *C12Q 3/00* | (2006.01) | |
| *G06T 7/44* | (2017.01) | |
| *G06T 7/62* | (2017.01) | |

(52) U.S. Cl.
CPC ............... *C12Q 3/00* (2013.01); *G06V 20/69* (2022.01); *G06T 7/44* (2017.01); *G06T 7/62* (2017.01); *G06T 2207/30242* (2013.01)

(56) References Cited

U.S. PATENT DOCUMENTS

| | | | |
|---|---|---|---|
| 8,889,406 B2 | 11/2014 | Van Der Heiden et al. | |
| 9,767,343 B1* | 9/2017 | Jones | G06V 20/698 |
| 2005/0186669 A1 | 8/2005 | Ho et al. | |
| 2009/0042293 A1* | 2/2009 | Hata | C12M 23/58 |
| | | | 382/133 |
| 2009/0111179 A1* | 4/2009 | Hata | C12M 23/48 |
| | | | 435/305.2 |
| 2012/0329151 A1* | 12/2012 | Baskar | C12M 29/20 |
| | | | 435/351 |
| 2013/0143307 A1* | 6/2013 | Nozaki | C12M 29/10 |
| | | | 435/286.1 |
| 2013/0316446 A1 | 11/2013 | Andersson et al. | |
| 2015/0072401 A1* | 3/2015 | Nozaki | C12M 37/00 |
| | | | 435/303.1 |
| 2015/0210971 A1 | 7/2015 | Baskar et al. | |
| 2016/0002584 A1* | 1/2016 | Nozaki | C12M 21/08 |
| | | | 435/289.1 |
| 2016/0017267 A1* | 1/2016 | Hansen | C12M 41/36 |
| | | | 435/29 |
| 2016/0115436 A1* | 4/2016 | Aijian | C12M 23/20 |
| | | | 435/173.9 |
| 2016/0272932 A1* | 9/2016 | Precht | C12M 41/12 |
| 2017/0088804 A1* | 3/2017 | Yoneda | C12M 21/08 |
| 2017/0166948 A1* | 6/2017 | Matsumoto | C12Q 1/02 |
| 2017/0191021 A1* | 7/2017 | Wakui | C12M 41/46 |
| 2017/0220000 A1* | 8/2017 | Ozcan | G03H 1/0443 |
| 2017/0260489 A1* | 9/2017 | Koseki | C12M 33/12 |
| 2017/0326549 A1* | 11/2017 | Jones | G01N 33/487 |
| 2018/0208958 A1* | 7/2018 | Drazek | C12Q 1/20 |
| 2019/0017009 A1* | 1/2019 | Yu | C12M 41/44 |
| 2019/0331905 A1* | 10/2019 | Shinoda | G06T 7/80 |

FOREIGN PATENT DOCUMENTS

| | | |
|---|---|---|
| JP | 2006-320226 | 11/2006 |
| WO | 2015/133116 | 9/2015 |

OTHER PUBLICATIONS

Database WPI, English abstract & figs. 1a & 1b of Japanese publication No. 2006320226, Week 200707; Thompson Scientific, London, GB; XP002776481, (2 pages).
Japanese Patent Office, Machine generated English Translation of JPH03-7575A, Published on Jan. 14, 1991 (12 pages).
European Patent Office, Machine generated English Translation of WO 2015/133116A1, published on Sep. 11, 2015 (12 pages).

* cited by examiner

SYSTEMS, APPARATUS AND METHODS FOR CONTROLLING A MOVEMENT OF A CELL CULTURE TO OPTIMIZE CELL GROWTH

CROSS-REFERENCE TO RELATED APPLICATION

This application is a continuation of U.S. patent application Ser. No. 15/703,500, filed Sep. 13, 2017, which in turn claims the benefit of U.S. Provisional Application Ser. No. 62/394,569 filed Sep. 14, 2016, the disclosure of which is incorporated herein by reference in their entirety.

TECHNICAL FIELD

The present invention relates generally to culturing cells, and more particularly, to systems, apparatus, and methods for controlling a movement of a cell culture to optimize cell growth.

BACKGROUND

The process of culturing cells requires providing nutritive components to an initial population of cells, whether from a pre-existing or recently isolated cell line, followed by incubation in a sterile vessel/container to facilitate cell proliferation. Existing cell culture methods include, for example, the cover glass method, the flask method, the rotating tube method and the like. Generally, a cell culture solution/media is used to promote the growth of the initial cell population by providing needed vitamins, amino acids and other nutrients to facilitate cell growth.

The culture of living cells makes it possible to obtain a cell population from a single cell, and may be performed for various purposes such as, for example, the recovery of additional by-products generated by cellular metabolism, the preparation of viral vaccines, cell generation to fabricate an artificial organ or to re-populate a de-cellularized organ scaffold, the production of pharmaceuticals by recombinant expression within eukaryotic (e.g., animal) cell lines, etc.

Typically, the process of cell culture requires a suitable container for culturing cells, a culture solution/media for supplying nutrition to the cells, and various gases, such as oxygen, to facilitate cell growth. The culture solution/media and various gases are introduced (e.g., injected) into the culture space of the container and used to culture cells. Examples of such culture solution/media include fetal bovine serum ("FBS") and bovine calf serum ("BCS"), although new regulatory trends lean toward minimizing or avoiding the use of FBS/BCS as a culture solution/medium. Periodically, the culture solution/media and the various gasses are replaced to maintain the cells in a fresh condition and to stimulate cell growth. In the alternative, culture solution/media and the various gasses are replaced on a continuous basis to maintain the cells in a fresh condition and to stimulate cell growth. By the continuous replacement of solution/media and the fine control of various gases, constant optimal levels of cell nutrients are obtained, and therefore FBS/BCS quantities are minimized, or new culture media that do not contain FBS/BCS can be adopted.

In addition, it is also desirable to ensure that cells growing in the culture space of the container are uniformly distributed to facilitate the supply of the culture solution/media and gases to the cells. However, in existing cell culture devices, the cells in the culture space often fail to grow in a uniformly distributed manner. For example, in many existing cell culture devices, cells grow in irregularly distributed patterns due to natural patterns of cell growth, the flow of the culture solution through the culture space of the container, or for other reasons not immediately known.

SUMMARY

In accordance with an embodiment, a method is provided. An image of a cell culture is generated, and a characteristic of the cell culture is determined based on the image. A movement of the cell culture is adjusted based on the characteristic to facilitate cell growth.

In one embodiment, motion data indicating a motion of a tray is received from a sensor. A first movement of the tray is determined based on the motion data. The movement of the cell culture is adjusted by determining a second movement of the tray based on the characteristic, the second movement being different from the first movement.

In another embodiment, the characteristic comprises a measure of cell density.

In another embodiment, a camera is used to capture an image of the cell culture, and the image data is analyzed to determine the measure of cell density.

In another embodiment, determining the measure of cell density includes determining a count of cell clusters. A determination is made whether the measure of cell density exceeds a predetermined limit, and the movement of the cell culture is adjusted in response to determining that the measure of cell density exceeds the predetermined limit.

In another embodiment, determining the measure of cell density includes determining one or more counts of cells representing cells with different morphologies. One or more measures of cell densities may be determined based on the one or more counts of cell morphologies.

In another embodiment, the cell culture is disposed in a tray with cells disposed either in adherence to the tray or in suspension in the culture solution. A tilting motion of the tray and/or a shaking motion of the tray is adjusted. Adjusting a tilting motion of the tray may include causing the tray to tilt back and forth at a lower or higher rate. Adjusting a shaking motion of the tray may include causing the tray to shake back and forth at a lower or higher rate.

In accordance with another embodiment, an apparatus includes a first device adapted to hold a cell culture container and to cause a movement of the cell culture in the container. The apparatus also includes a second device adapted to generate an image of the cell culture in the container, and at least one processor adapted to determine a characteristic of the cell culture based on the image, and to cause the first device to adjust the movement of the cell culture container, based on the characteristic.

In one embodiment, the characteristic comprises a measure of cell density.

In one embodiment, the characteristic comprises at least one measure of cell density determined based on a determination of different cell morphologies.

In another embodiment, the processor is further adapted to determine a measure of average cell density based on the image.

In accordance with another embodiment, a system includes a tray adapted to hold a cell culture container, a camera adapted to capture an image of the cell culture within the container, and a device adapted to control a movement of the tray. The system also includes a processor adapted to determine a first movement of the tray, receive from the camera data representing an image of the cell culture, determine a characteristic of the cell culture based on the image data, determine a second movement of the tray based on the characteristic, the second movement being different from the first movement, and cause the device to cause the tray to move in accordance with the second movement.

In one embodiment, the system also includes a sensor adapted to obtain motion data indicating a motion of the tray. The processor is further adapted to receive the motion data from the sensor and determine the first movement of the tray based on the motion data.

In another embodiment, the characteristic comprises a measure of cell density.

In another embodiment, the processor is further adapted to determine a measure of cell density based on the image data.

In another embodiment, the processor is further adapted to determine a count of cell clusters, and determine the measure of cell density based on the count of cell clusters.

In another embodiment, the processor is further adapted to determine that the measure of cell density exceeds a predetermined limit, and determine the second movement in response to the determination that that the measure of cell density exceeds the predetermined limit.

In another embodiment, the processor is further adapted to determine one or more different morphologies of cells in a culture, determine one or more counts of cells having different characteristics such as shape, size, etc., and determine one or more measures of cell densities according to the different cell types.

In another embodiment, the processor is further adapted to adjust one of a tilting motion of the tray and a shaking motion of the tray to determine the second movement of the tray. The processor may be adapted to cause the tray to tilt back and forth at a lower or higher rate or to cause the tray to shake back and forth at a lower or higher rate.

These and other advantages of the present disclosure will be apparent to those of ordinary skill in the art by reference to the following Detailed Description and the accompanying drawings.

DETAILED DESCRIPTION

In accordance with an embodiment, a cell culture system includes a first device adapted to hold a cell culture and to cause the cell culture to move in a manner selected to optimize cell growth. The apparatus also includes a second device adapted to generate an image of the cell culture, and at least one processor adapted to determine a characteristic of the cell culture based on the image, and to cause the first device to adjust the movement of the cell culture, based on the characteristic.

Figure 1:
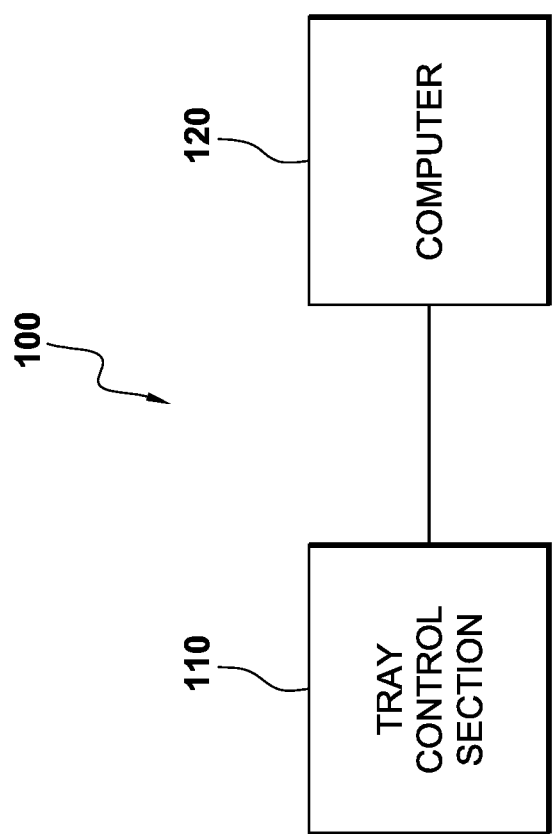
FIG. 1 shows components of a cell culture system in accordance with an embodiment.

FIG. 1 shows components of a cell culture system in accordance with an embodiment. Cell culture system 100 includes a tray control system 110 and a computer 120. Tray control system 110 is adapted to hold a cell culture and to move the cell culture in a manner that facilitates and optimizes cell growth. Computer 120 may receive data from tray control system 110 and may transmit control signals to tray control system 110. Computer 120 may be any suitable processing device such as a server computer, a personal computer, a laptop device, a cell phone, etc.

Figure 2:
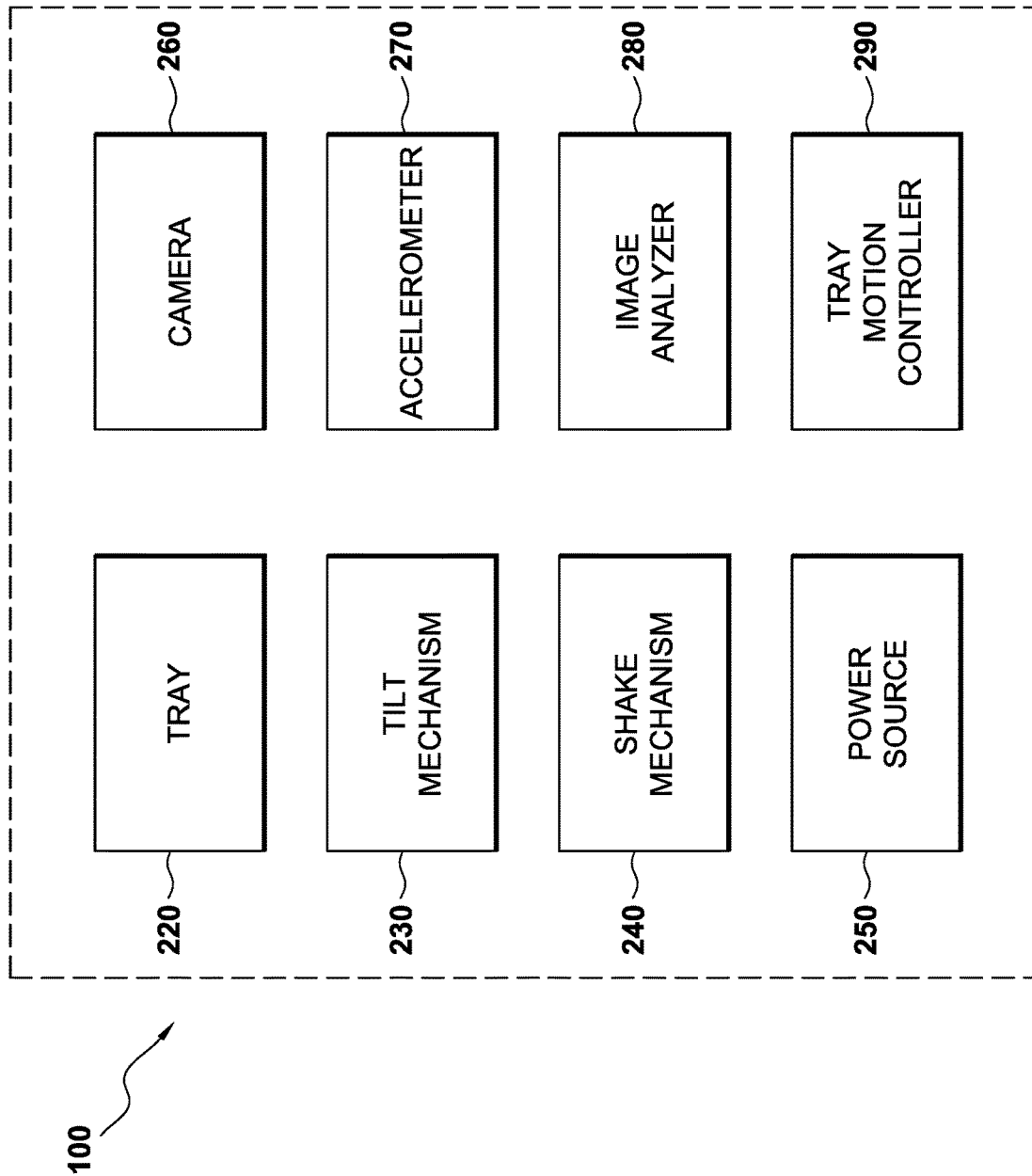
FIG. 2 shows components of a cell culture system in accordance with another embodiment.

FIG. 2 shows components of cell culture system 100 in accordance with another embodiment. Cell culture system 100 includes a tray 220, a tilt mechanism 230, a shake mechanism 240, a power source 250, a camera 260, an accelerometer 270, an image analyzer 280, and a tray motion controller 290. Cell culture system 100 may include components not shown in FIG. 2.

Tray 220 includes a surface adapted to hold a cell culture. Tray 220 may have any shape; tray 220 may be square, rectangular, circular, or another shape. Tray 220 may include more than one surface. In one embodiment, a cell culture is contained in a container disposed directly on the surface of tray 220. In another embodiment, a cell culture may be contained in a bag, or other enclosure that is disposed on tray 220. Tray 220 may be made from plastic (including transparent plastics), metal, or any other suitable material.

Tilt mechanism 230 causes tray 220 to tilt, i.e., to change its orientation from a horizontal position (wherein tray 220 is disposed in a horizontal plane) to a selected non-horizontal position (wherein tray is disposed in a second non-horizontal plane). For example, tilt mechanism 230 may cause tray 220 to move back and forth between a first non-horizontal plane (defined by a first predetermined angle relative to the horizontal plane) and a second non-horizontal plane (defined by a second predetermined angle relative to the horizontal plane) at a selected speed or acceleration. Tilt mechanism 230 may operate in response to control signals received from a processing device.

Shake mechanism 240 causes tray 220 to shake, i.e., to move from side to side at a selected speed or acceleration. Shake mechanism 240 may operate in response to control signals received from a processing device.

Power source 250 provides power to cell culture system 100. For example, power source 250 may include one or more batteries. Cell culture system 100 may include more than one power source.

Camera 260 obtains images of a cell culture disposed on tray 220. Camera 260 may be a digital camera, for example. Camera 260 may provide digital image data to a computer or other processing device for analysis.

Accelerometer 270 is a sensor adapted to obtain data indicating the acceleration of tray 220. Accelerometer 270 may also measure other parameters including the speed and/or other motions of tray 220, for example. Accelerometer 270 may provide acceleration and/or other motion data to a computer or other processing device.

In other embodiments, cell culture system 100 may include other types of sensors such as sensors to measure temperature, mass, weight, pH, gas levels ($O_2$ and $CO_2$), etc.

Image analyzer 280 analyzes image data generated by camera 260 and determines one or more characteristics of the cell culture disposed on tray 220. For example, image analyzer 280 may analyze an image of a cell culture and determine a measure of cell density. Image analyzer 280 may transmit information (e.g., a measure of cell density or other information) to tray motion controller 290.

Tray motion controller 290 controls the motion of tray 220. For example, tray motion controller 290 may cause tilt mechanism 230 to tilt tray 220. Tray motion controller 290 may cause shake mechanism 240 to shake tray 220. From time to time, tray motion controller 290 may receive information from image analyzer 280 and, based on the information, cause tilt mechanism 230 or shake mechanism 240 to adjust the motion of tray 220. For example, tray motion controller 290 may receive from image analyzer 280 a measure of cell density (which may include, for example, a measure of average cell density, one or more measures of cell densities according to different cell morphologies, etc.) and, based on the measure of cell density, causing tilt mechanism 230 or shake mechanism 240 to adjust the motion of tray 220.

One or more components shown in FIG. 2 may be implemented by a computer such as computer 120 of FIG. 1. For example, image analyzer 280 and/or tray motion controller 290 may comprise software (and/or circuitry) residing and operating on computer 120.

Figure 3A:
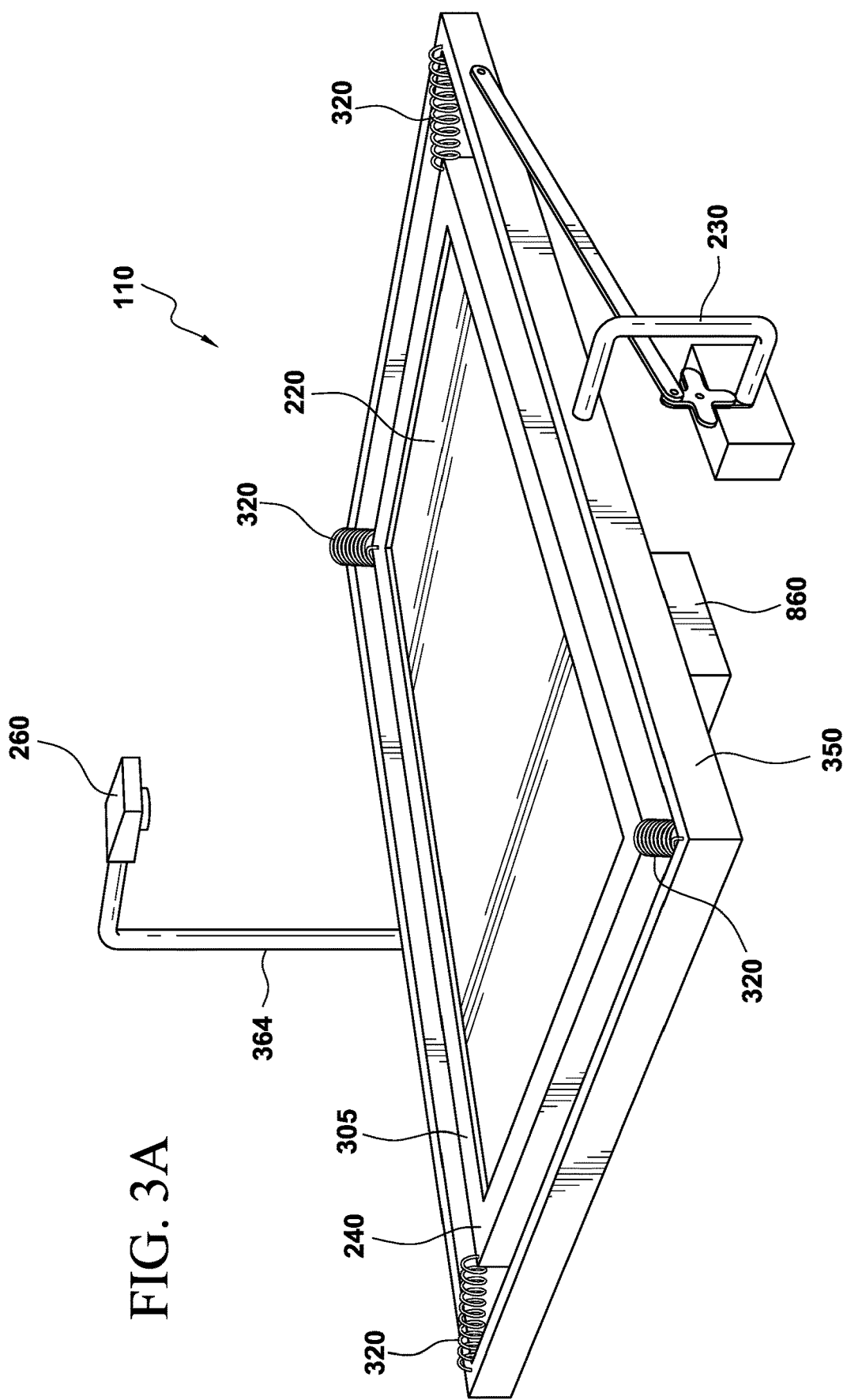
FIG. 3A shows a perspective view of a tray control system in accordance with an embodiment.

FIG. 3A shows a perspective view of tray control system 110 in accordance with an embodiment. Tray control system 110 includes a frame 350. Shake mechanism 240 includes a rectangular plate 305 which is disposed within frame 350 and is coupled to frame 350 by four coils 320. Tray 220 is disposed on a top surface of shake mechanism 240. Shake mechanism 240 also includes a shake controller 860 (located underneath plate 305). Tilt mechanism 230 is connected to a side of frame 350. Camera 260 is positioned above tray 220 by an arm 364, which may be connected to a side of frame 350, for example.

Figure 3B:
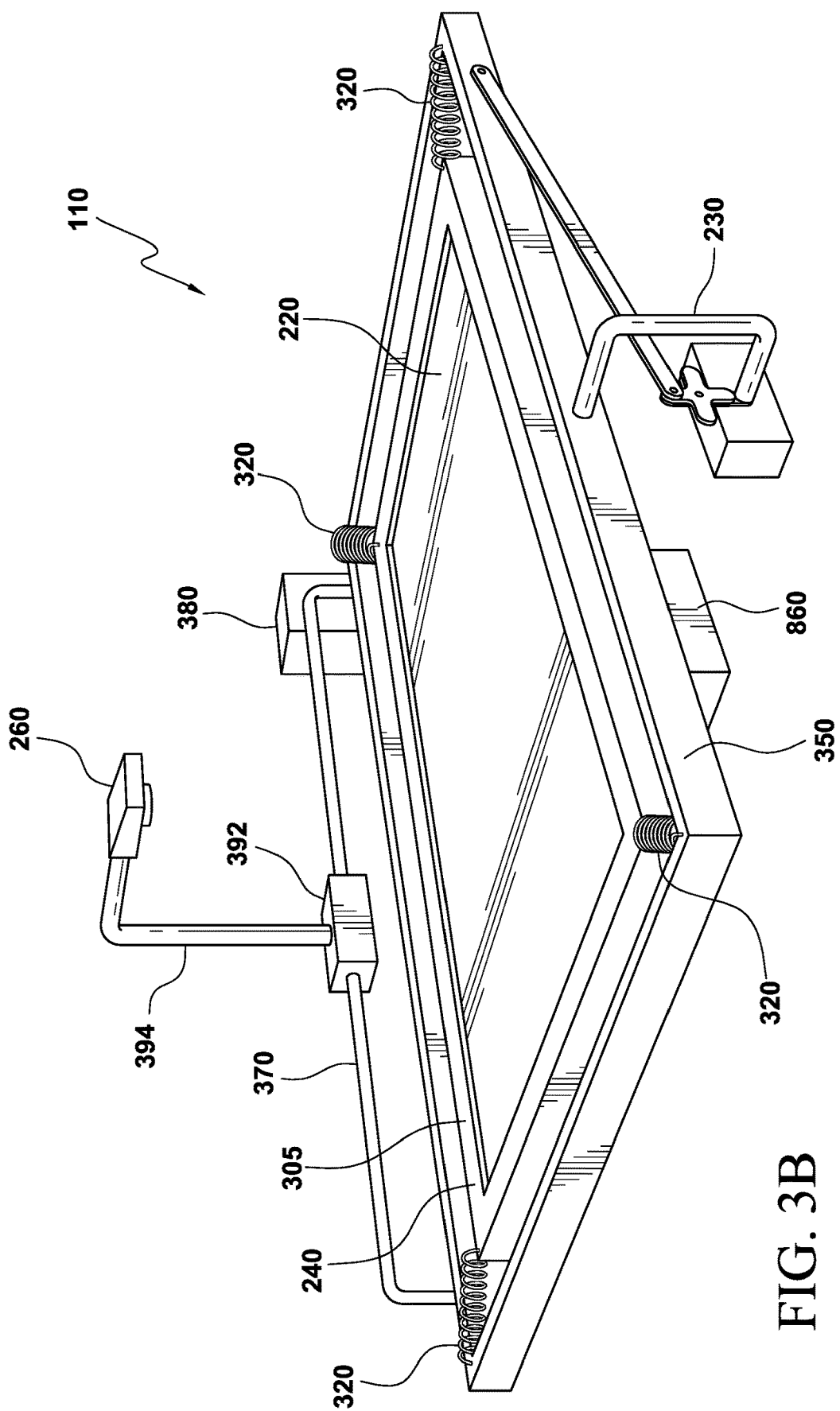
FIG. 3B shows a perspective view of a tray control system in accordance with another embodiment.

FIG. 3B shows a perspective view of tray control system 110 in accordance with another embodiment. Tray control system 110 includes frame 350, shake mechanism 240, and rectangular plate 305. Tray 220 is disposed on the top surface of shake mechanism 240. Tilt mechanism 230 is connected to the side of frame 350. A rod 370 is positioned above one side of frame 350. A sliding mechanism 392 is adapted to slide along rod 370. Sliding mechanism 392 is connected to and supports an arm 394, which holds camera 260 above tray 220. Because arm 394 is connected to sliding mechanism 392, the camera 260 may be moved from one end of frame 350 to the other end, to obtain various views of tray 220 (and various views of any culture located on tray 220). Tray control system 110 also includes a controller 380 adapted to control the movement of sliding mechanism 392. Thus, controller 380 is adapted to cause camera 260 to move from a first position to a second, selected position to obtain an image of a selected portion of tray 220.

Figure 4:
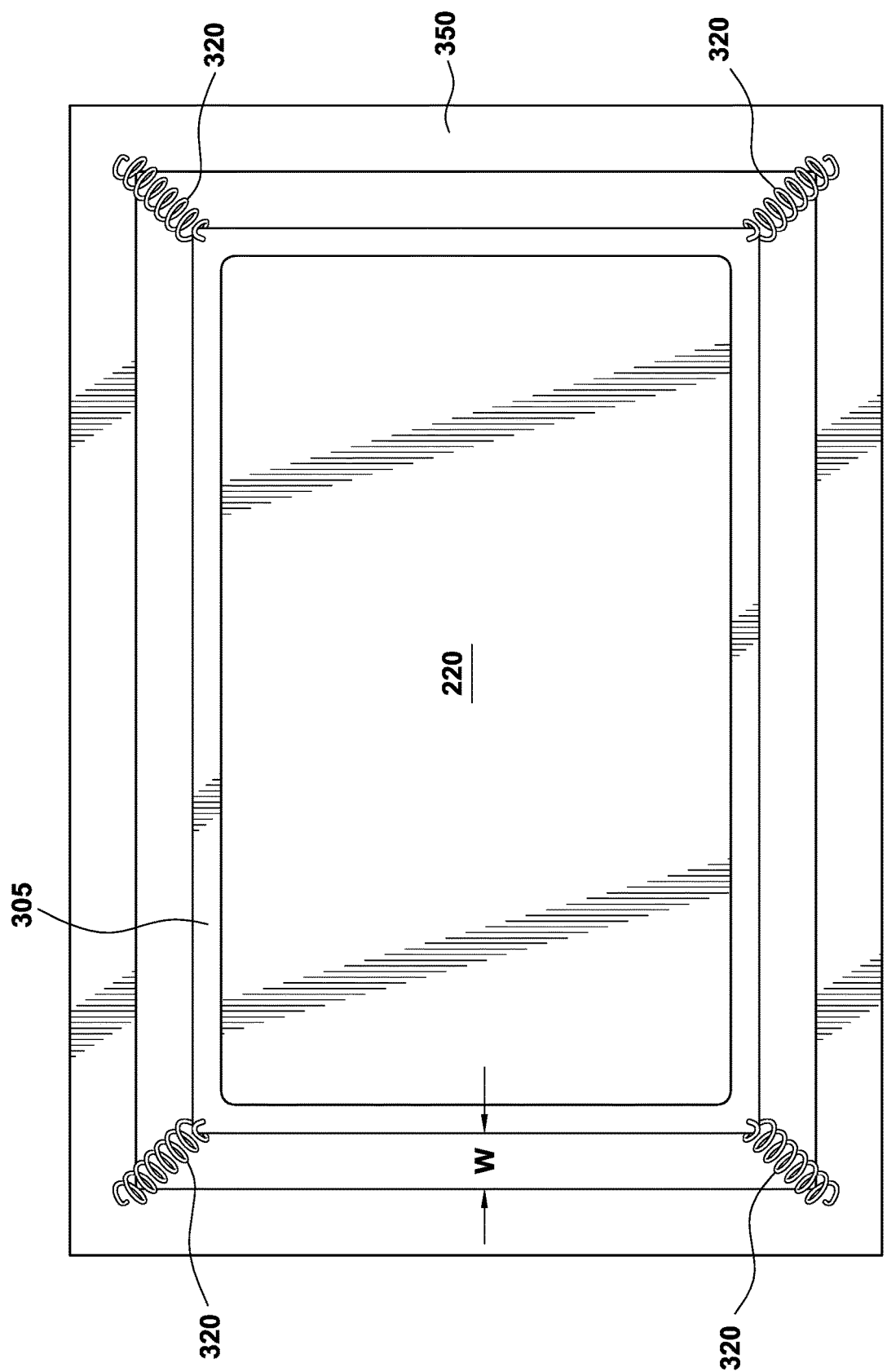
FIG. 4 shows a top view of the frame, plate, and tray of the embodiment of FIG. 3.

FIG. 4 shows a top view of frame 350, plate 305, and tray 220 of the embodiment of FIG. 3. Plate 305 is separated from frame 350 by a gap of width "W". The gap between plate 305 and frame 350 allows plate 305 (and tray 220, which is disposed on plate 305) to move within frame 350. In one embodiment, width "W" is between 5.0-20.0 millimeters.

Figure 5:
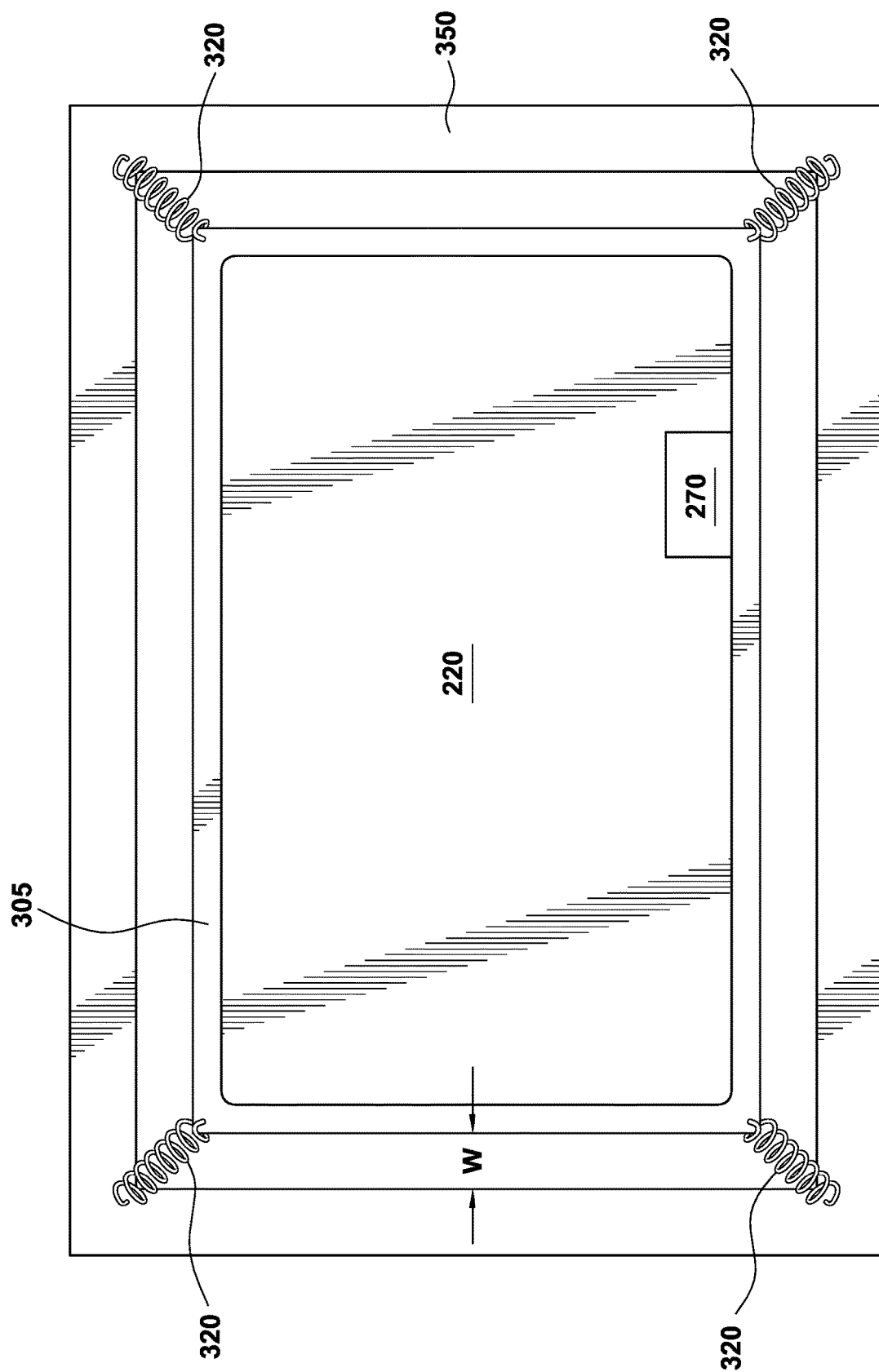
FIG. 5 shows a top view of a frame, plate, and tray in accordance with another embodiment.

FIG. 5 shows a top view of frame 350, plate 305, and tray 220 in accordance with another embodiment. Accelerometer 270 is disposed on tray 220. In other embodiments, accelerometer 270 may be placed in another location or position.

In accordance with an embodiment, a cell culture within a container is disposed on tray 220, and the motion of the cell culture is controlled to optimize cell growth. The motion of the cell culture may be controlled by controlling the motion of tray 220, for example. Specifically, tray 220 may tilt back and forth. Alternatively, tray 220 may shake in a back-and-forth motion. Moving tray 220 in such a motion causes the cell culture disposed on tray 220 to move in a similar motion. Moving the cell culture should cause the distribution of cells in the cell culture to change; for example, a rapid tilting or shaking motion may cause cells that are in clusters to separate, thereby decreasing the cell density within the cell culture. Advantageously, decreasing the cell density may facilitate the growth of cells in the cell culture. However, movement of tray 220 should be regulated to avoid excessive shear within the cell culture that can lead to disruption of the cell membrane and unwanted cell death.

Figure 6A:
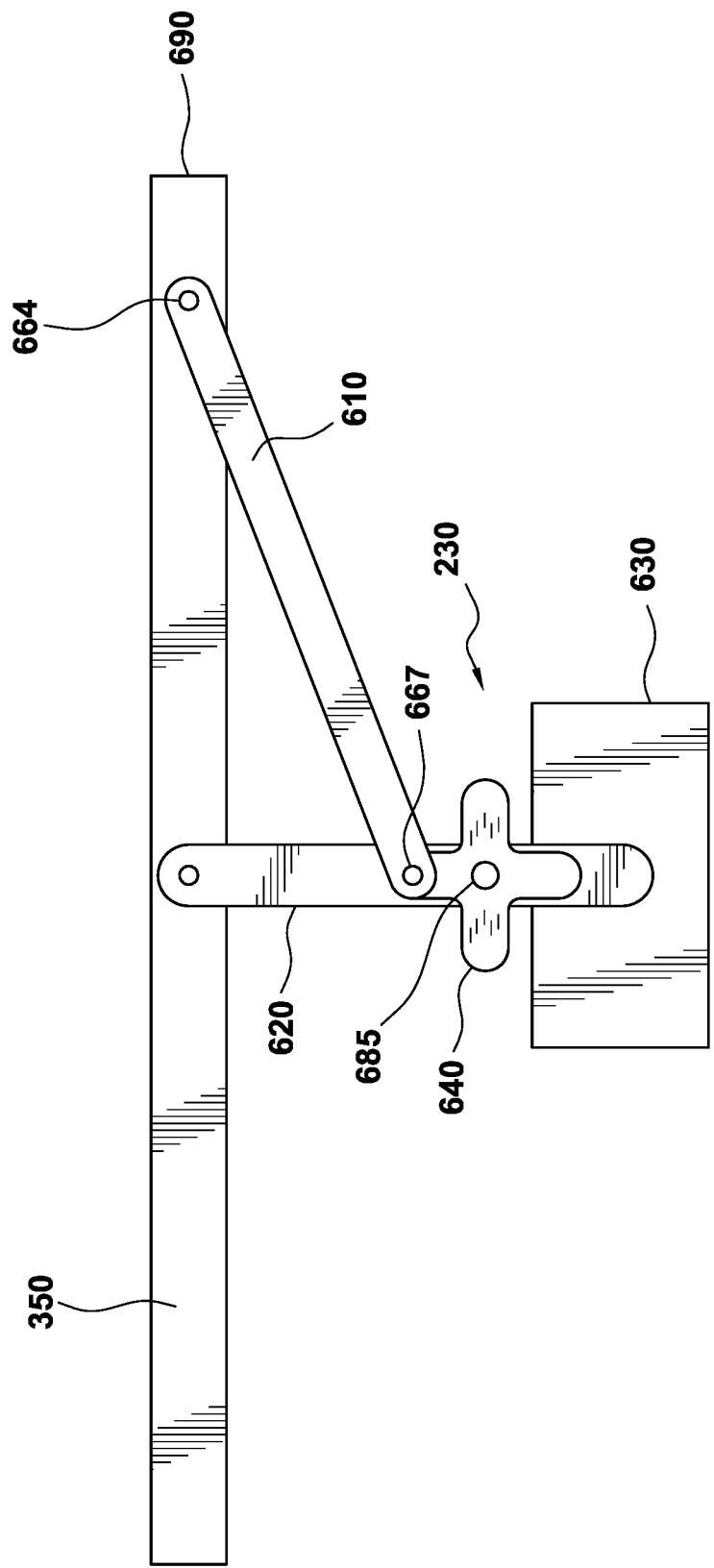
FIGS. 6A-6C show the operation of a tilt mechanism in accordance with an embodiment.
Figure 6B:
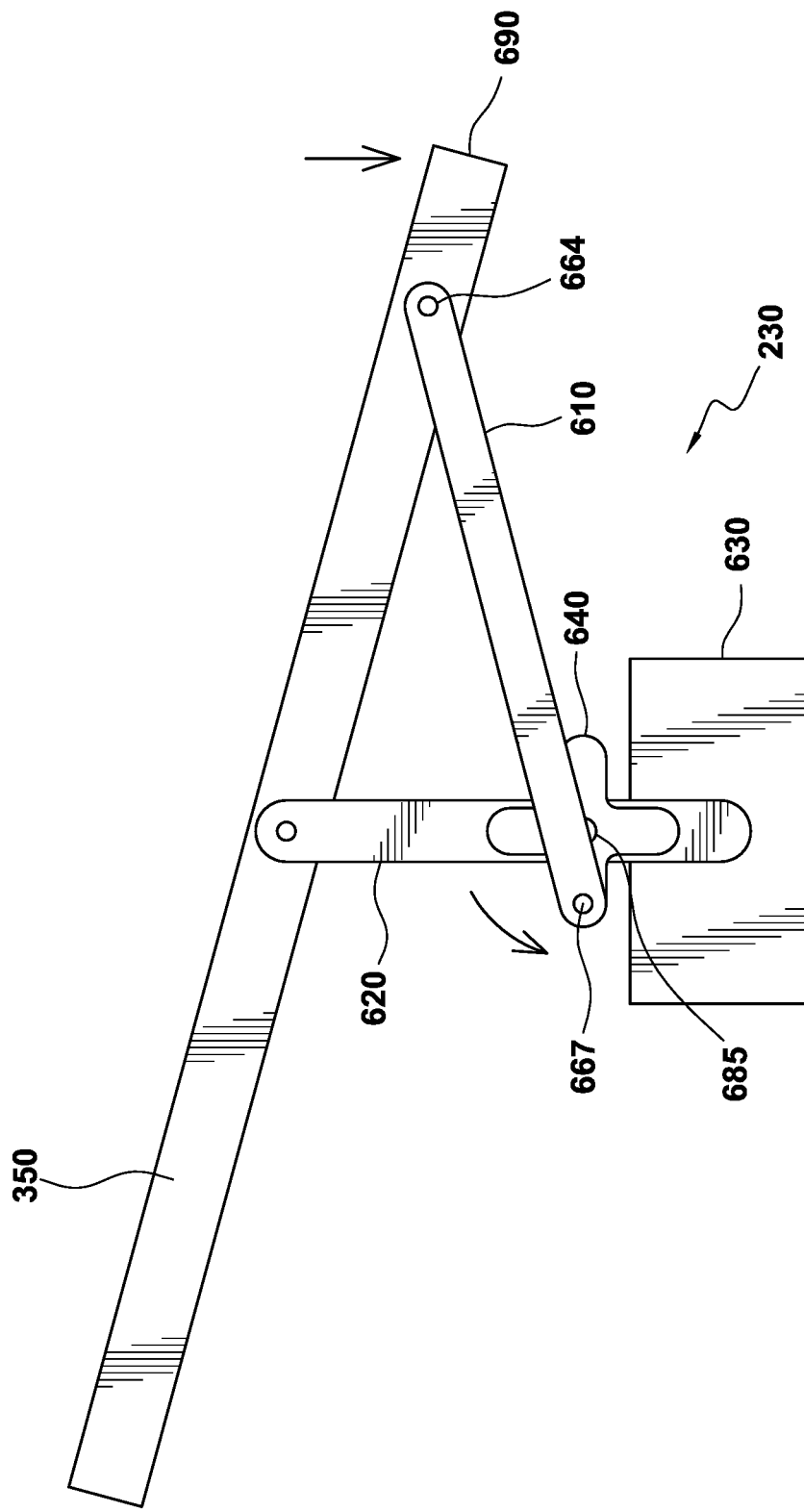
Figure 6C:
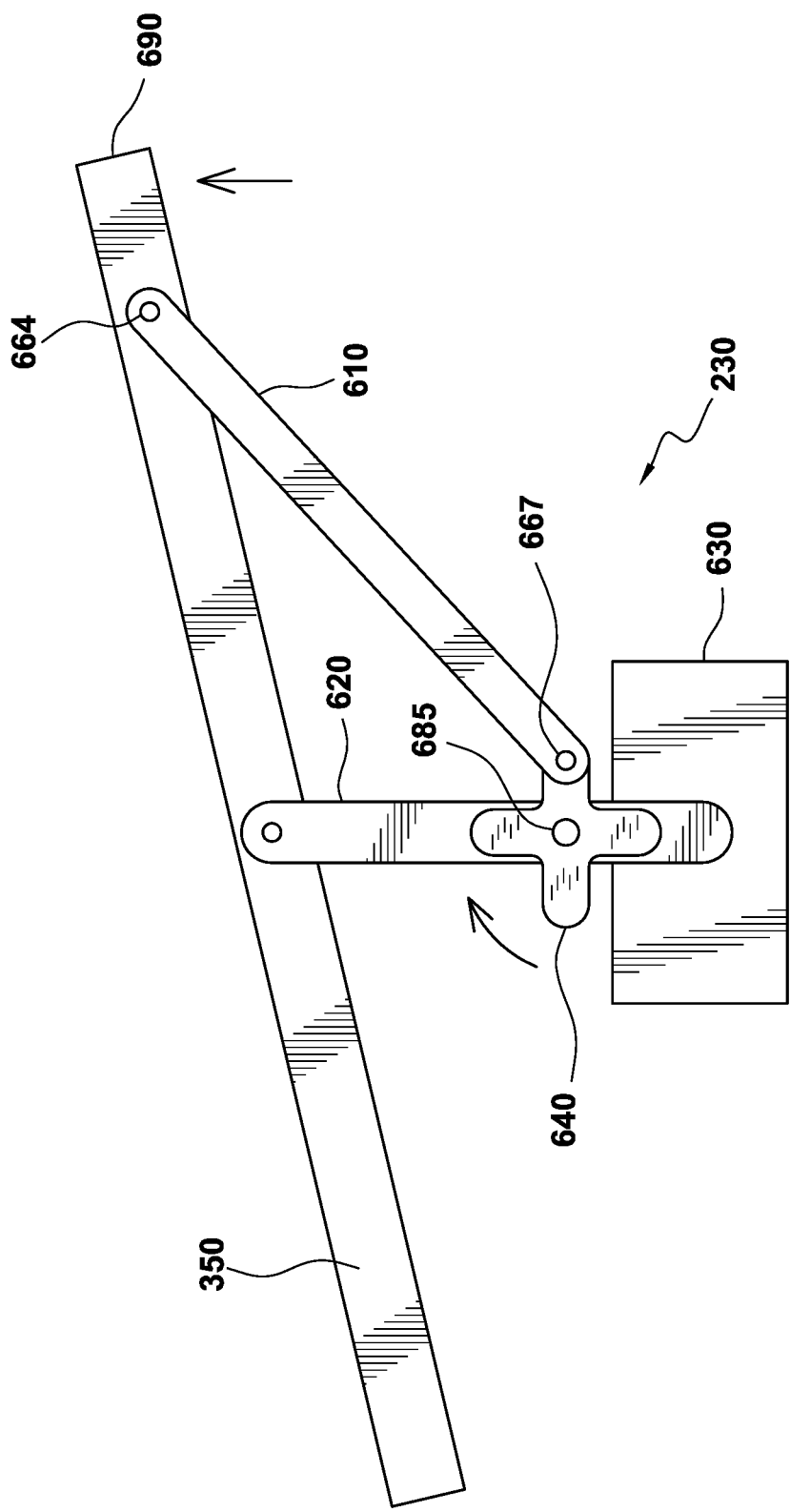

FIGS. 6A-6C show the operation of tilt mechanism 230 in accordance with an embodiment. Referring to FIG. 6A, tilt mechanism 230 includes a support arm 620 connected to frame 350. A tilt controller 630 is attached to support arm 620. A rotating piece 640, which has four rotating arms, is attached to support arm 620 and is controlled by tilt controller 630. A lever 610 is connected at a first end to one of the rotating arms of rotating piece 640 by a connector 667 and at a second end to frame by a second connector 664. Connectors 664 and 667 may be screws, for example, or another type of fastener.

Referring to FIG. 6B, tilt controller 630 from time to time causes rotating piece 640 to rotate in a counter-clockwise direction. When rotating piece 640 rotates in a counter-clockwise direction, rotating piece 640 pulls lever 610, which in turn causes an end 690 of frame 350 to tilt downward. When frame 350 tilts to one side, plate 240 and tray 220 also tilt in a similar manner.

Referring now to FIG. 6C, tilt controller 630 from time to time causes rotating piece 640 to rotate in a clockwise direction. When rotating piece 640 rotates in a clockwise direction, rotating piece 640 pushes lever 610, which in turn causes end 690 of frame 350 to tilt upward. When frame 350 tilts to one side, plate 240 and tray 220 also tilt in a similar manner.

Figure 6D:
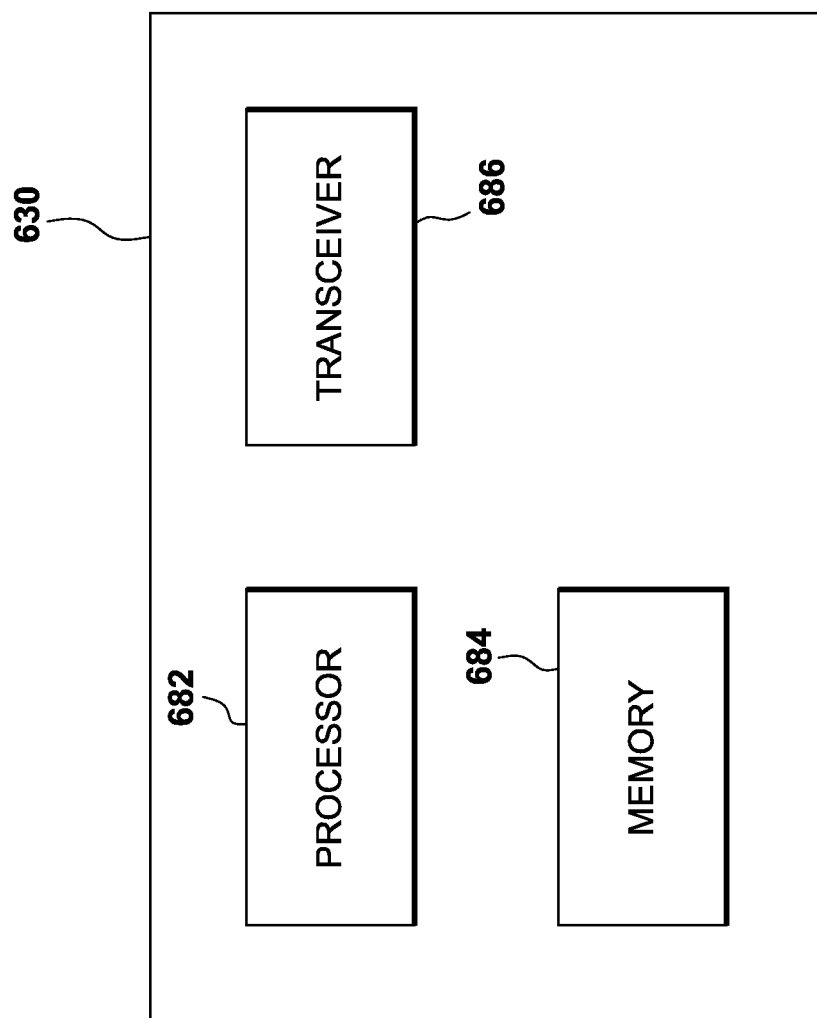
FIG. 6D shows components of a tilt controller in accordance with an embodiment.

FIG. 6D shows components of tilt controller 630 in accordance with an embodiment. Tilt controller 630 includes a processor 682, a memory 684, and a transceiver 686. Processor 682 controls the movement of rotating piece 640. Processor 682 may from time to time store data in memory 684. Transceiver 686 may from time to time receive control signals (e.g., from tray motion controller 290 or from other components). Transceiver 686 may include an antenna, for example.

Figure 7:
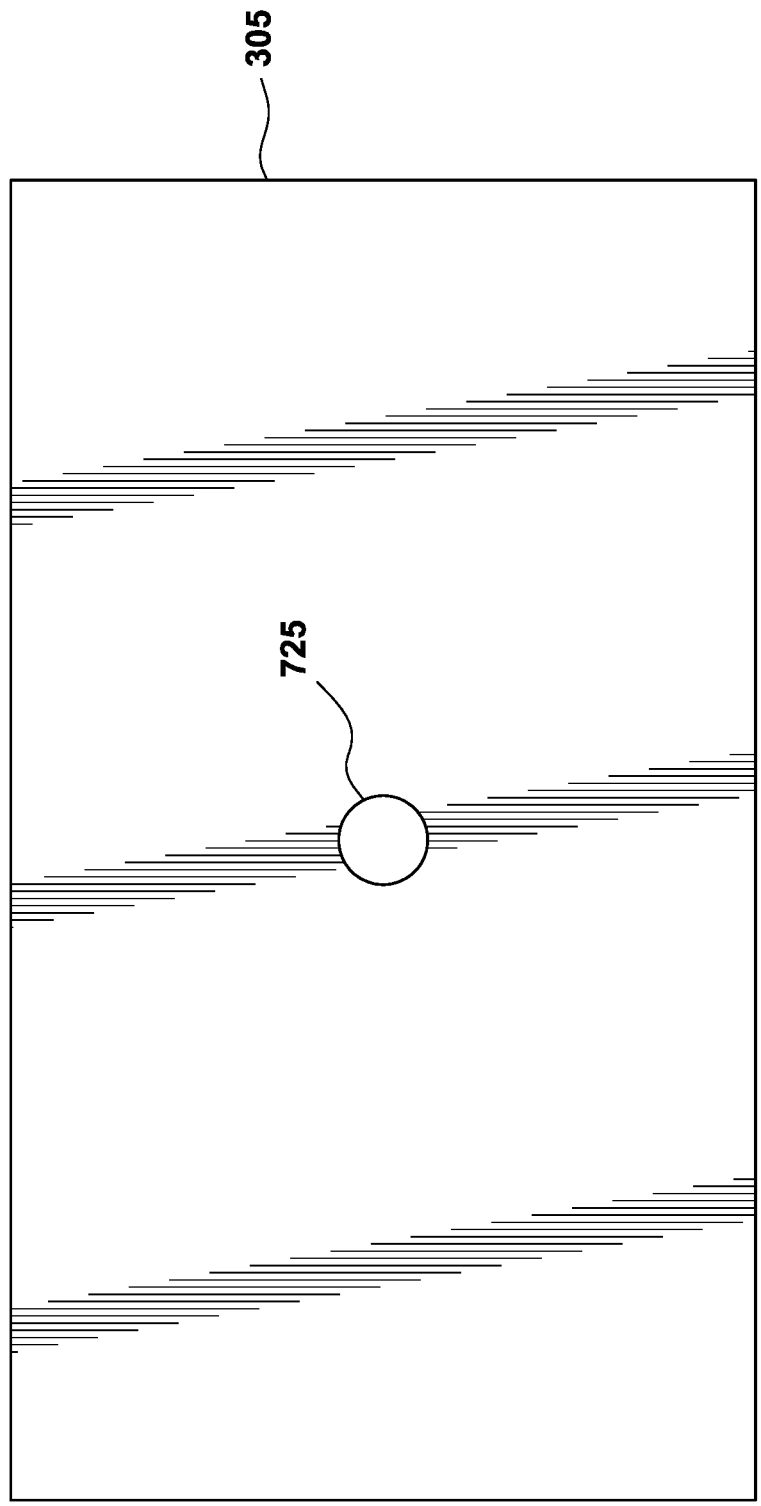
FIG. 7 shows a top view of the plate of the embodiment of FIG. 3.

Referring again to FIG. 3, tray 220 rests on plate 305. FIG. 7 shows a top view of plate 305 in accordance with an embodiment. Plate 305 has hole 725 at or near the center of the plate. Hole 725 passes through plate 305. Plate 305 may be made from plastic, metal, or another suitable material. Plastics may include transparent plastics, which allow transmitted light mode imaging. Thus, in one embodiment, tray 220 may comprise a transparent plastic, plate 305 may also comprise a transparent plastic; in such case, transparent light mode imaging may be used. Hole 725 may have a diameter between 1.0 centimeters and 5.0 centimeters, for example. Other diameters may be used.

Figure 8A:
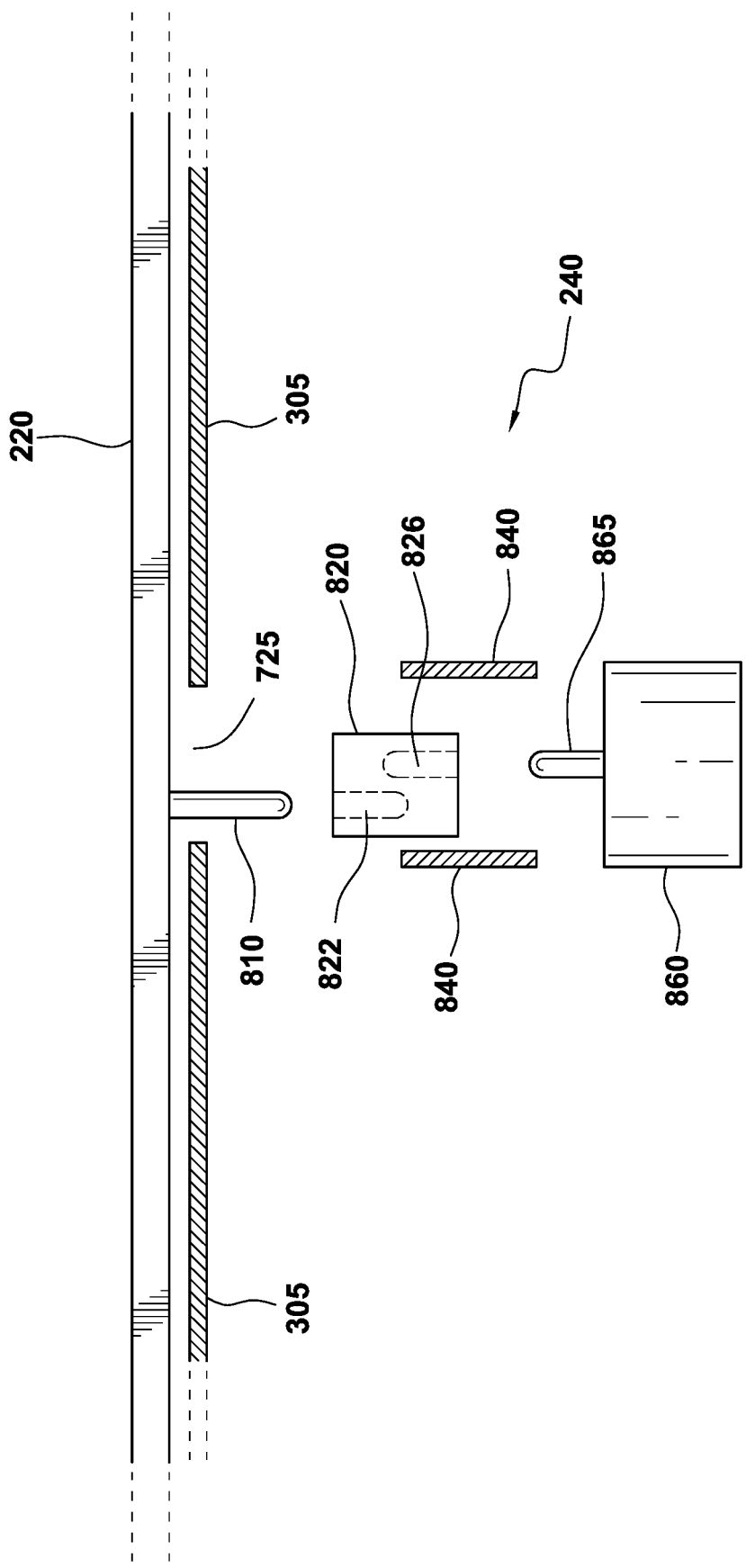
FIGS. 8A-8C show the operation of a shake mechanism in accordance with an embodiment.
Figure 8B:
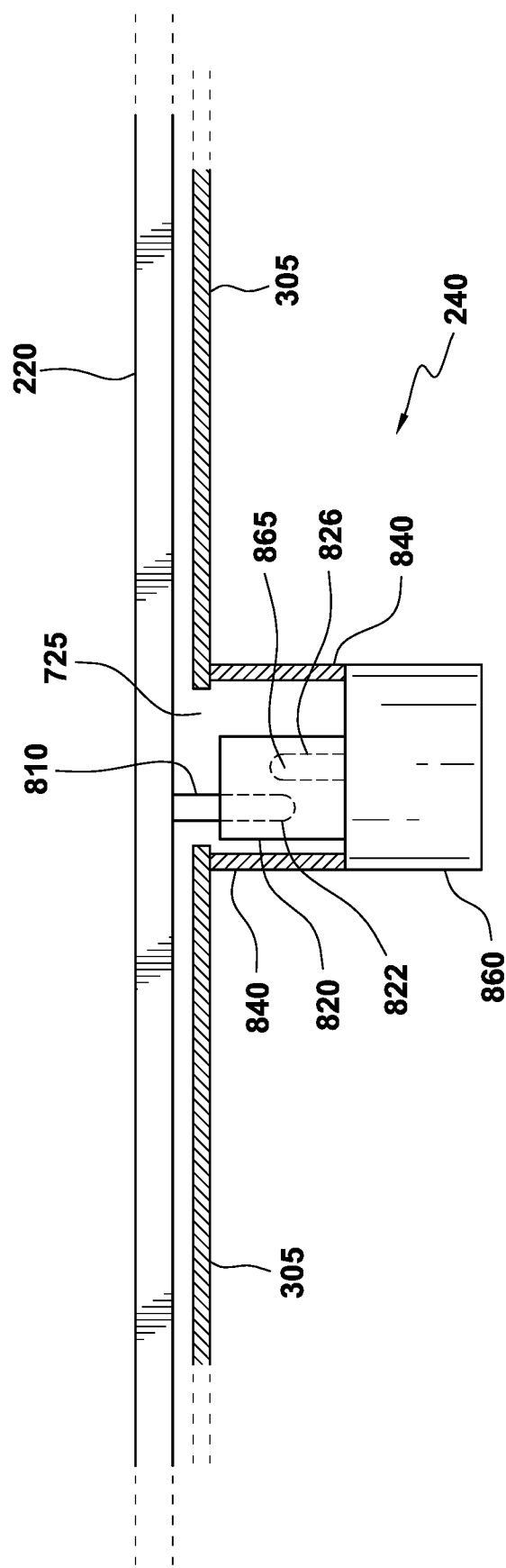
Figure 8C:
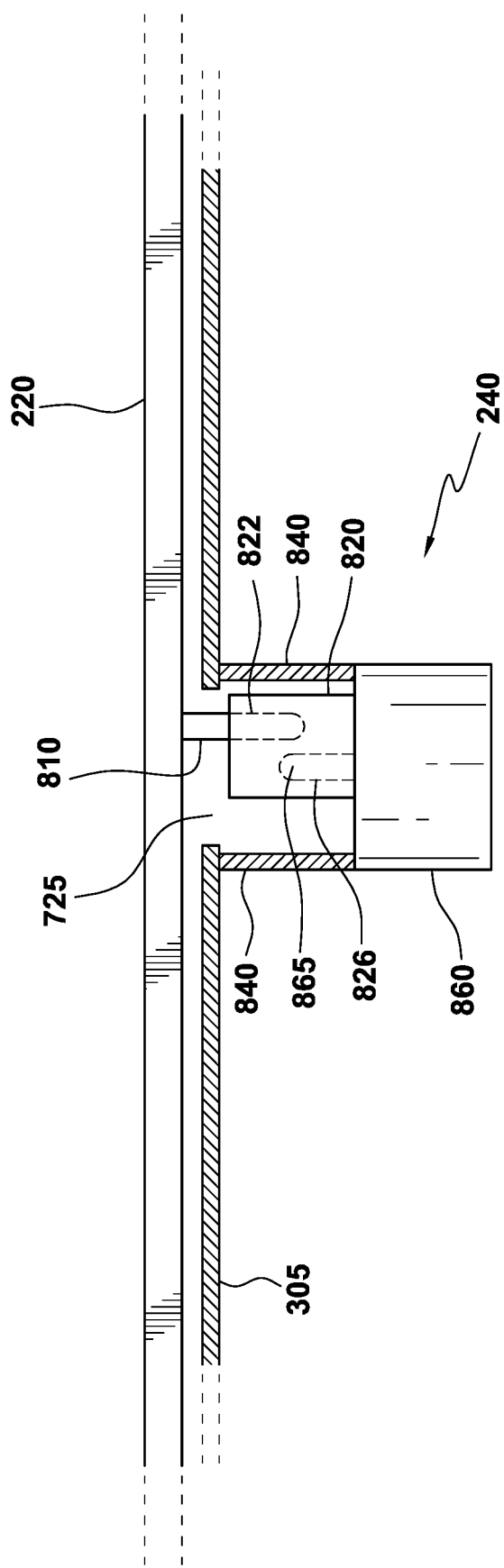

FIGS. 8A-8C show the operation of shake mechanism 240 in accordance with an embodiment. FIG. 8A shows a cross-sectional view of tray 220 and components of shake mechanism 240. Tray 220 rests on plate 305. Tray 220 includes a projecting member 810 which projects from the underside of tray 220 and fits through hole 725.

Shake mechanism 240 includes a rotating piece 820, shake controller 860, and one or more connectors 840. Rotating piece 820 includes a first cavity 822 and a second cavity 826. Shake controller 860 has a spinning member 865.

Referring to FIG. 8B, projecting member 810 of tray 220 fits into first cavity 822 of rotating piece 820. Spinning member 865 of shake controller 860 fits into second cavity 826 of rotating piece 820. Connectors 840 connect shake controller 860 to plate 305. In other embodiments, other types of connectors may be used to connect shake controller 860 to plate 305. For example, shake controller 860 may be held in a basket which is connected to plate 305.

In accordance with an embodiment, shake controller 860 causes spinning member 865 to spin. Spinning member 865 is fixed within cavity 826 of rotating piece 820. Consequently, as spinning member 865 spins, it causes rotating piece 820 to rotate around spinning member 865, thereby causing projecting member 810 of tray 220 to rotate in a circle within hole 725. FIG. 8C shows tray 220 and the components of shake mechanism 240 after rotating piece has rotated approximately one hundred eighty (180) degrees relative to the position shown in FIG. 8B. This motion has caused projecting member 810, and tray 220, to move.

In one embodiment, shake controller 860 may cause spinning member 865 to spin at between 10 and 300 rotations per second. Other rates of rotation may be used. The rotating motion of projecting member 810 causes tray 220 to move in a circular motion on top of plate 305. The circular motion of tray 220 imparts a shaking motion to any cell culture disposed on tray 220.

Figure 8D:
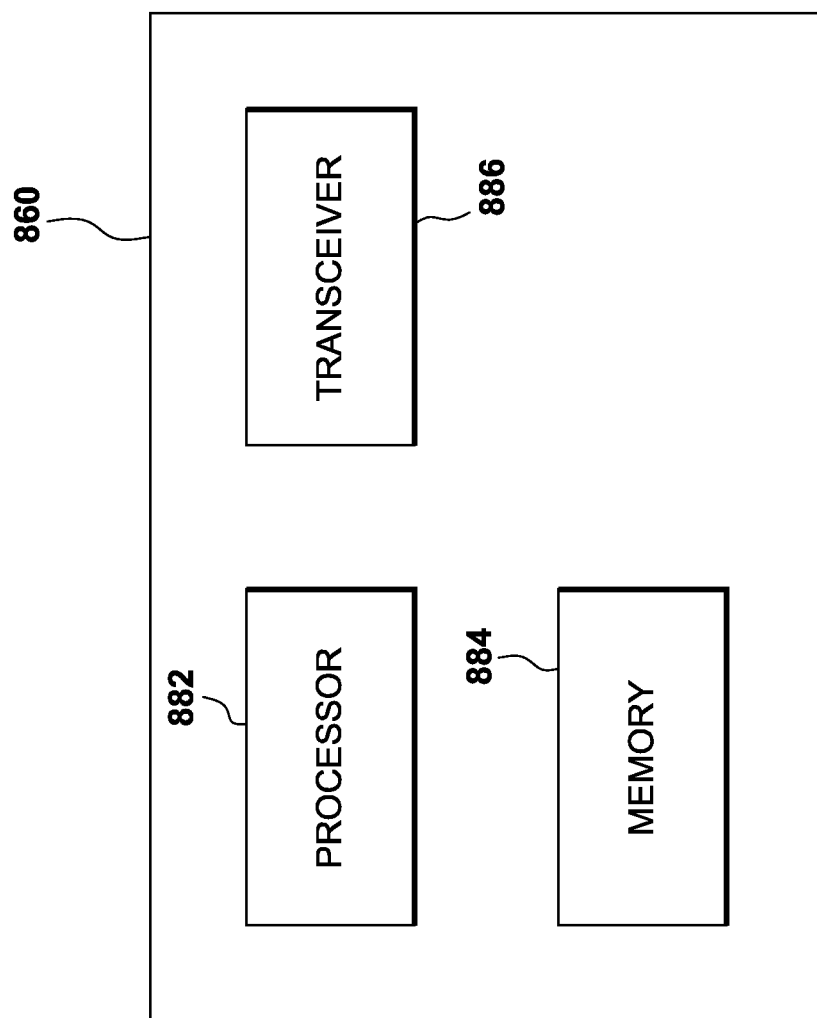
FIG. 8D shows components of a shake controller in accordance with an embodiment.

FIG. 8D shows components of shake controller 860 in accordance with an embodiment. Shake controller 860 includes a processor 882, a memory 884, and a transceiver 886. Processor 882 controls the movement of spinning member 865. Processor 882 may from time to time store data in memory 884. Transceiver 886 may from time to time receive control signals (e.g., from tray motion controller 290 or from other components). Transceiver 886 may include an antenna, for example.

Figure 9:
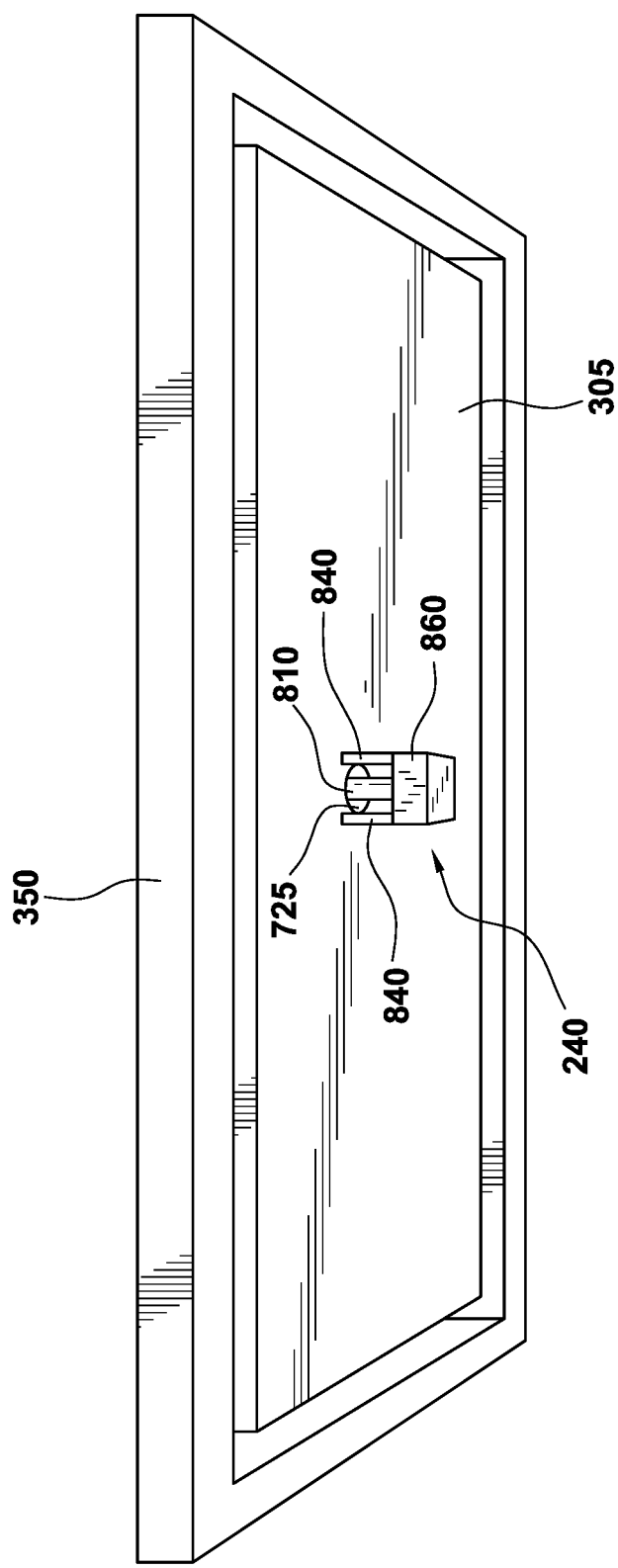
FIG. 9 shows a perspective view of the underside of the frame, plate, and shake mechanism of the embodiment of FIGS. 8A-8C.

FIG. 9 shows a perspective view of the underside of frame 350, plate 305, and shake mechanism 240 of the embodiment of FIGS. 8A-8C. In other embodiments, shake mechanism 240 may be configured differently and/or may operate in a different manner.

In accordance with an embodiment, cell culture system 100 may be used to optimize cell growth in a cell culture. Cell culture system 100 can be a batch reactor system, a fed batch reactor system or a continuous reactor system. Such systems are well known in the art. Cell culture system 100 can also be modularized for ease of use.

In an illustrative example, a container containing a cell culture is placed on tray 220, and the tray is moved in accordance with a predetermined pattern. For example, the tray may be tilted back and forth at a first selected rate in order to facilitate a uniform distribution of cells. One or more images of the cells are captured. Motion data indicating the motion of the tray is also obtained. The image data is analyzed to determine a measure of cell density within the cell culture. An adjusted motion of the tray is determined based on the image data and the motion data. For example, supposing that the measure of cell density is determined to exceed a predetermined limit, an adjusted motion selected to decrease cell density may be determined. For example, the adjusted motion may include tilting the tray at a second selected rate (faster than the first rate) and/or at a selected angle, and may further include shaking the tray at a third selected rate. The tray is then caused to move in accordance with the adjusted motion.

Figure 10:
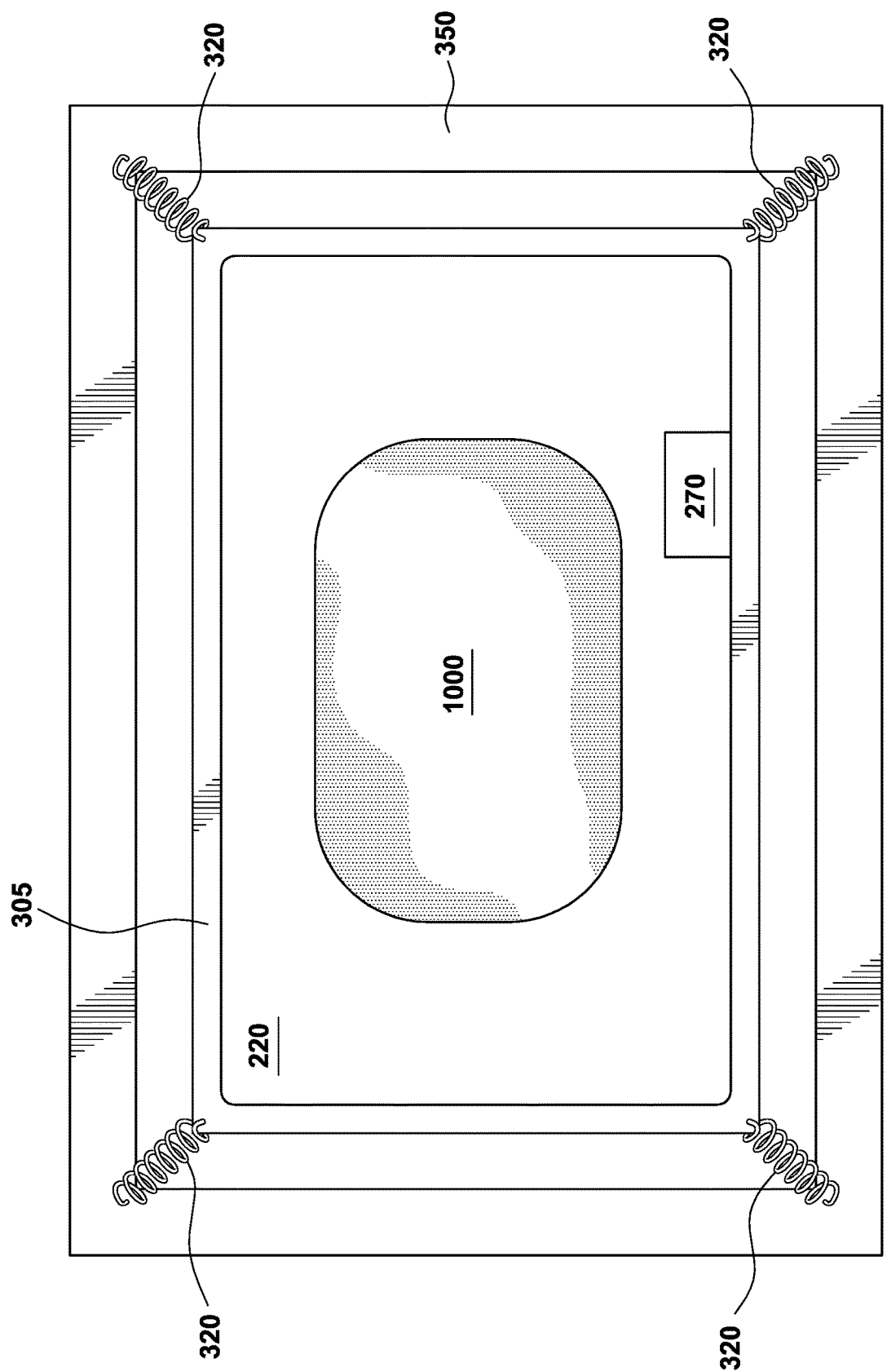
FIG. 10 shows a cell culture disposed on a tray in accordance with an embodiment.

For example, in an illustrative embodiment shown in FIG. 10, a cell culture 1000 is disposed on tray 220. Tray motion controller 290 now uses tilt mechanism 230 and shake mechanism 240 to cause tray 220 to follow a predetermined motion. For example, tilt mechanism 230 and shake mechanism 240 may be used to cause tray 220 to tilt back and forth at a first predetermined rate, and to shake back and forth at a second predetermined rate.

Cell culture system 100 is now used to monitor cell growth in cell culture 1000 and control (and adjust) the motion of tray 220 in order to optimize the cell growth. For example, cell growth may be facilitated by determining if an undesirably high level of cell density occurs in the cell culture and, in response, adjusting the motion of tray 220 to facilitate cell growth within the cell culture in a manner that reduces the cell density.

Figure 11A:
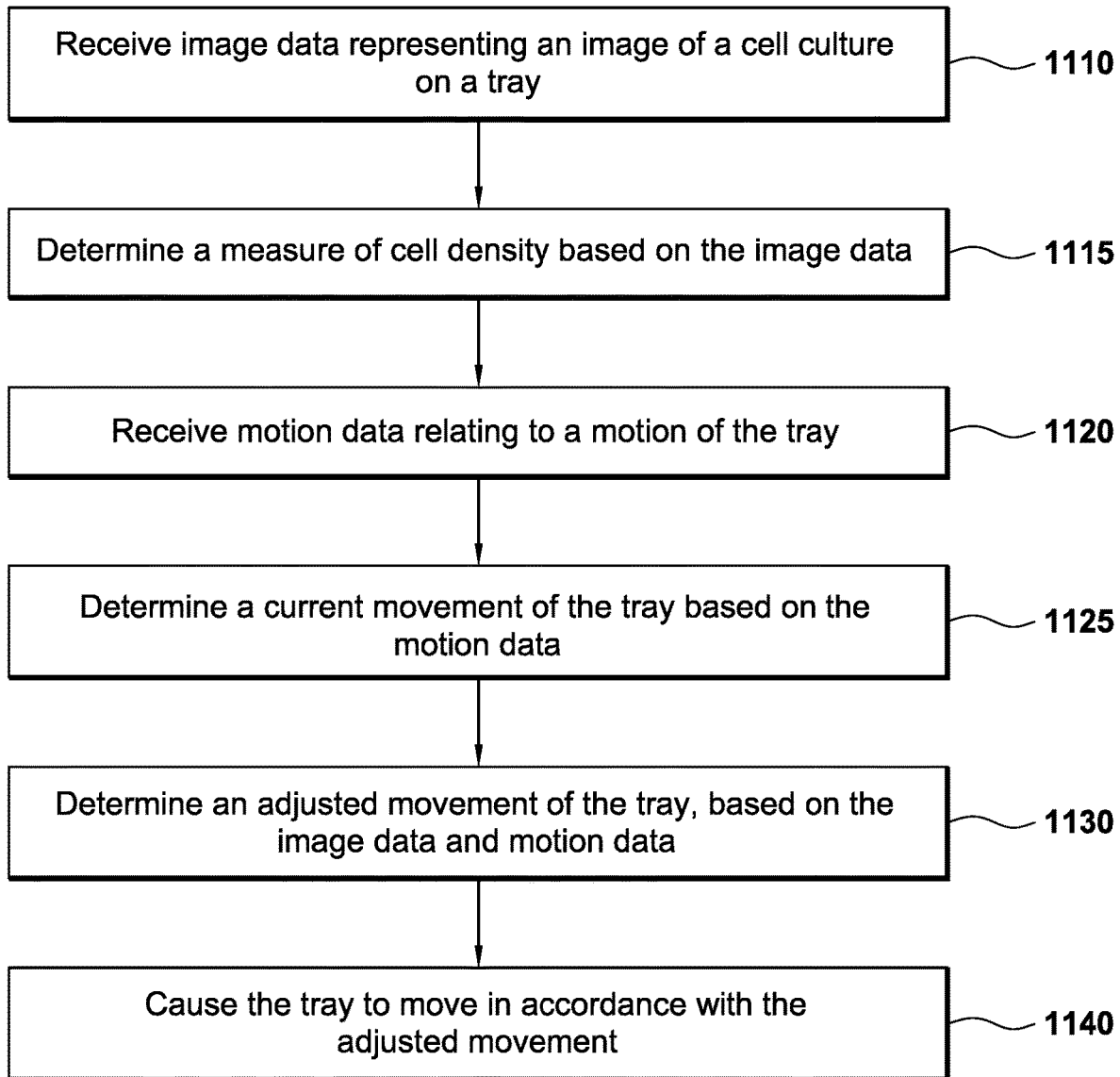
FIG. 11A is a flowchart of a method of controlling a movement of a tray in accordance with an embodiment.

FIG. 11A is a flowchart of a method of controlling a motion of a cell culture in accordance with an embodiment. At step 1110, image data representing an image of a cell culture on a tray is received. In the illustrative embodiment, camera 260 captures one or more images of cell culture 1000. Camera 260 converts the image into image data and transmits the image data to image analyzer 280.

At step 1115, a measure of cell density is determined based on the image data. Image analyzer 280 receives the image data from camera 260 and analyzes the image data to generate a measure of cell density. Any one of a variety of methods may be used to generate a measure of cell density. For example, image analyzer 280 may identify all cells in the image and calculate a measure of average cell density. In another embodiment, image data may be used to identify different cell morphologies (size, shape, etc.) among the cells in the cell culture and determine one or more measures of cell densities based on the different cell morphologies. Alternatively, image analyzer 280 may examine cells in the cell culture to identify features that meet predetermined criteria. For example, image analyzer 280 may identify regions where "cell clusters" are forming, wherein a "cluster" is defined as a region having a cell density above a predetermined limit. Image analyzer 280 may then use a count of the number of such regions as a measure of cell density. Other measures may be used. The measure of cell density is provided to tray motion controller 290.

At step 1120, motion data relating to a motion of the tray is received. In the illustrative embodiment, accelerometer 270 generates motion data and transmits the motion data to tray motion controller 290. The motion data may include, without limitation, data indicating acceleration, speed, direction of motion, etc. Tray motion controller 290 may receive multiple measurements of motion over a selected period of time.

At step 1125, a current movement of the tray is determined based on the motion data. Tray motion controller 290 analyzes the motion data received from accelerometer 270 and determines a current movement of tray 220. For example, tray motion controller 290 may determine, based on the motion data, that tray 220 is at rest, or that tray 220 is moving in a particular direction at a particular speed and acceleration, or that tray 220 is following a pattern of motion such as a back-and-forth motion, etc.

At step 1130, an adjusted movement of the tray is determined, based on the image data and motion data. In the illustrative embodiment, tray motion controller 290 analyzes the cell density information and the motion data and determines whether an adjustment to the tray's movement is desirable in order to optimize or improve cell growth. Supposing that tray motion controller 290 determines that an adjusted movement is required, the adjustment to the tray's movement may include an adjustment to the tilting motion of tray 220 and/or an adjustment to the horizontal (shaking) movement of tray 220. For example, tray motion controller 290 may determine that cell density exceeds a predetermined limit and, in response, determine that the tilting motion of tray 220 should be adjusted by tilting the tray to a higher angle, and/or by tilting the tray back and forth at a higher rate, or may determine that the shaking motion of tray 220 should be adjusted by shaking the tray at a higher rate, etc.

At step 1140, the tray is caused to move in accordance with the adjusted movement. Tray motion controller 290 causes tilt mechanism 230 and shake mechanism 240 to adjust the tray's motion in order to effect the adjusted movement determined at step 1130. Thus, tray motion controller 290 may cause tilt mechanism 230 to tilt tray 220 at a faster or slower rate, for example, and/or may cause shake mechanism 240 to shake tray 220 at a faster or slower rate. For example, tray motion controller 290 may generate and transmit control signals to tilt mechanism 230 and/or to shake mechanism 240 to effect the adjusted movement.

In other embodiments, other characteristics of a cell culture disposed on tray 220 may be determined and used to adjust the motion of the tray. For example, image analyzer 280 and/or one or more sensors may be used to determine, without limitation, a measure of a color of a cell culture, a measure of a temperature of a cell culture, a measure of a weight of a cell culture, one or more measures of different cell densities according to different cell morphologies, a measure of transparency or opaqueness of a cell culture, etc., may be determined. Alternatively, patterns of cell growth may be determined from the image data. Adjustments to the motion of tray 220 may be determined and applied based on these observed and measured characteristics.

In another embodiment, a measure of cell density may be determined by examining an image of a cell culture and defining one or more "cell areas" containing one or more cells. For example, two cells that are located within a predetermined distance of another cell may be considered to be within the same cell area. An outline is defined around the perimeter of each cell area. The total area occupied by cell areas is determined. A measure of cell density may then be determined based on the total area occupied by cell areas, with respect to the area not occupied by cell areas. For example, a measure of cell density may be determined as a ratio of the total area occupied by cell areas to the total area of the tray (or that portion of the tray covered by the cell culture). Alternatively, a measure of cell density may be determined by comparing the total area occupied by cell areas to a predetermined value.

In another embodiment, a measure of cell density may be determined based on an observed quantity of cell nuclei for eukaryotic cell cultures. For example, an image of a cell culture may be examined to identify each cell nucleus in the image. A measure of cell density for the eukaryotic cell may be determined based on the observed quantity of cell nuclei.

In another embodiment, a measure of cell density is determined by analyzing pixels in an image of the cell culture. A first quantity of edge pixels, and a second quantity of non-edge pixels, are determined. A measure of cell density may be determined, for example, by determining a ratio of edge pixels to non-edge pixels.

In other embodiments, an image recognition algorithm may be used to identify features such as patterns of cell growth, different cell densities according to different cell morphologies, etc. A measure of cell density may be determined based on an analysis of cell growth features.

In another embodiment, a Voronoi algorithm may be used to determine a measure of cell density.

In another embodiment, a measure of cell density may be determined based on an overlap measurement.

In another embodiment, a measure of cell density may be determined based on a measurement of cell movement. For example, a trajectory of one or more cells may be observed and analyzed. A measure of cell density may be determined based on the observed movements and trajectories.

In another embodiment, a measure of cell density may be determined based on RGB measurements.

In another embodiment, a measure of cell density may be determined based on HSV measurements.

In another embodiment, a measure of cell density may be determined based on grey scale conversion.

In another embodiment, a measure of cell density may be determined based on color channel gradients.

In another embodiment, a measure of cell density may be determined based on index of refraction measurements.

In another embodiment, a measure of cell density may be determined based on temperature measurements. For example, the temperature of a cell culture may be measured and a measure of cell density may be determined based on the temperature measurement.

In another embodiment, a measure of cell density may be determined based on mass measurements of mass. For example, the mass of a cell culture may be measured and a measure of cell density may be determined based on the mass measurement.

In another embodiment, a measure of cell density may be determined based on weight measurements. For example, the weight of a cell culture may be measured and a measure of cell density may be determined based on the weight measurement.

In another embodiment, a measure of cell density may be determined based on phase measurements. For example, a wave front sensor may be used to detect a wave front.

In another embodiment, a measure of cell density may be determined based on spectrum measurements.

In another embodiment, a measure of cell density may be determined based on observations of cell type and/or cell shape.

In another embodiment, a measure of cell density may be determined based on other methods, such as dielectric spectroscopy, light absorption, light scattering, Fourier transform image analysis, etc.

Figure 11B:
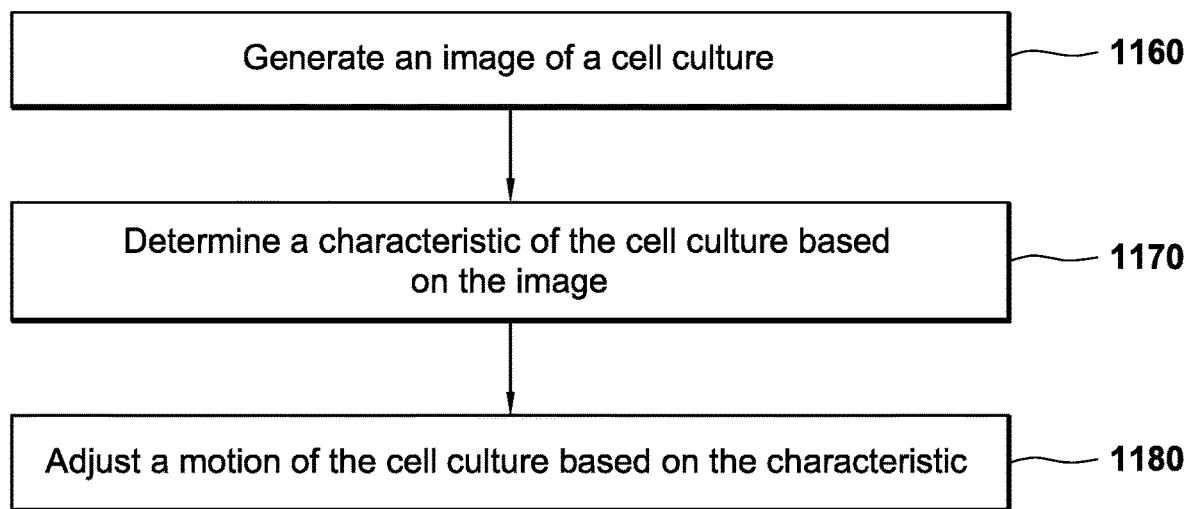
FIG. 11B is a flowchart of a method of controlling a movement of a cell culture in accordance with another embodiment.

FIG. 11B is a flowchart of a method of controlling a motion of a cell culture in accordance with another embodiment. At step 1160, an image of a cell culture is generated. As described herein, camera 260 may obtain an image of a cell culture disposed in tray 220.

At step 1170, a characteristic of the cell culture is determined based on the image. Image analyzer 280 and/or tray motion controller 290 may determine any desired characteristic based on the image data, such as cell density, color, growth patterns, etc.

At step 1180, a motion of the cell culture is adjusted based on the characteristic. Because the cell culture is disposed on tray 220, the motion of the cell culture is adjusted by adjusting the movement of tray 220. In a manner similar to those described herein, tray motion controller 290 may cause tilt mechanism 230 and/or shake mechanism 240 to adjust the motion of tray 220, based on the determined characteristic. For example, the motion of tray 220 may be adjusted to optimize cell growth based on a measured cell density, a measured color, an observed pattern of cell growth, etc. Tray 220 moves in accordance with the adjusted motion, causing the cell culture to move as well.

Figure 12A:
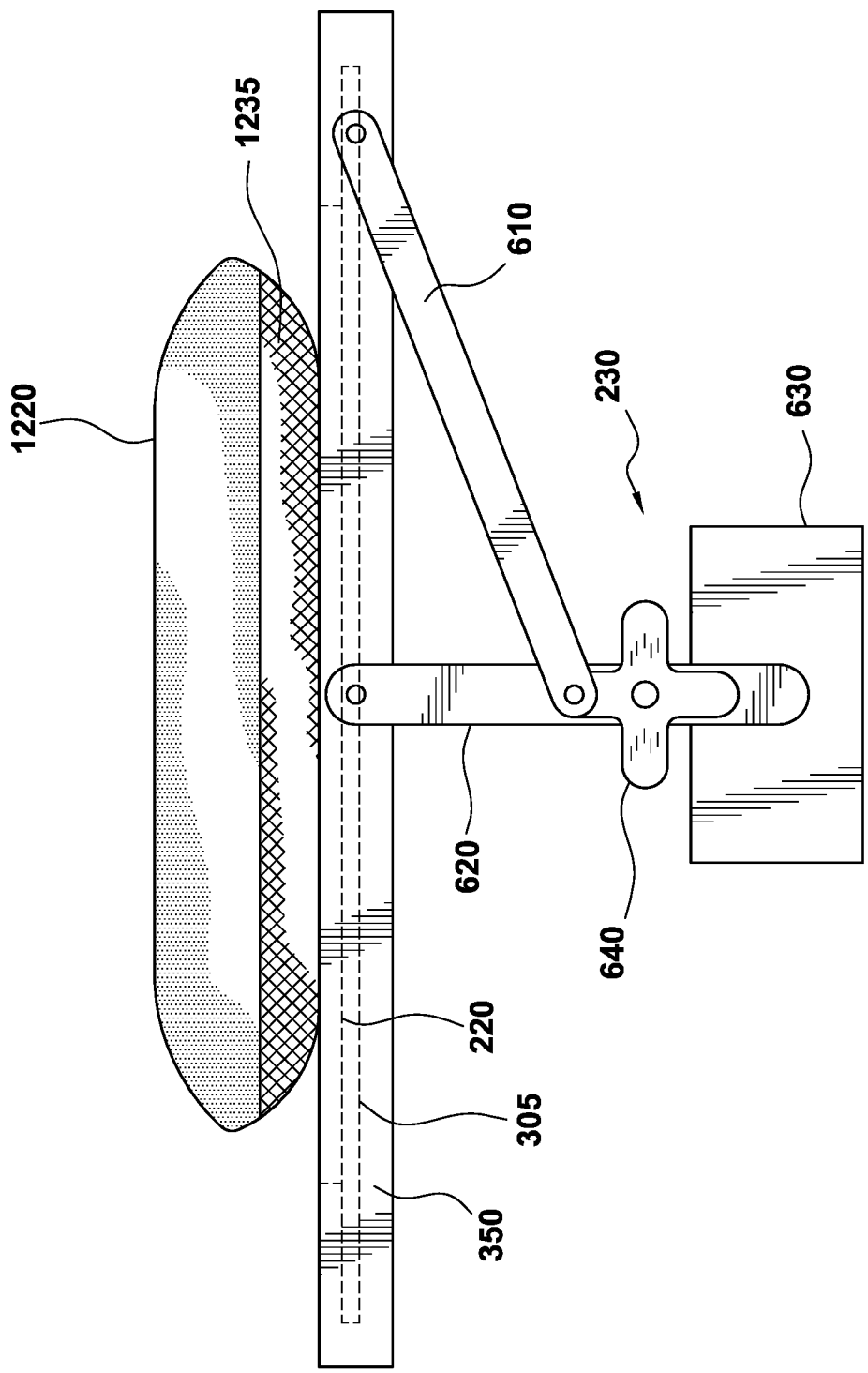
FIG. 12A shows a side view of a frame and tilt mechanism supporting a bag with cell culture in accordance with an embodiment.
Figure 12B:
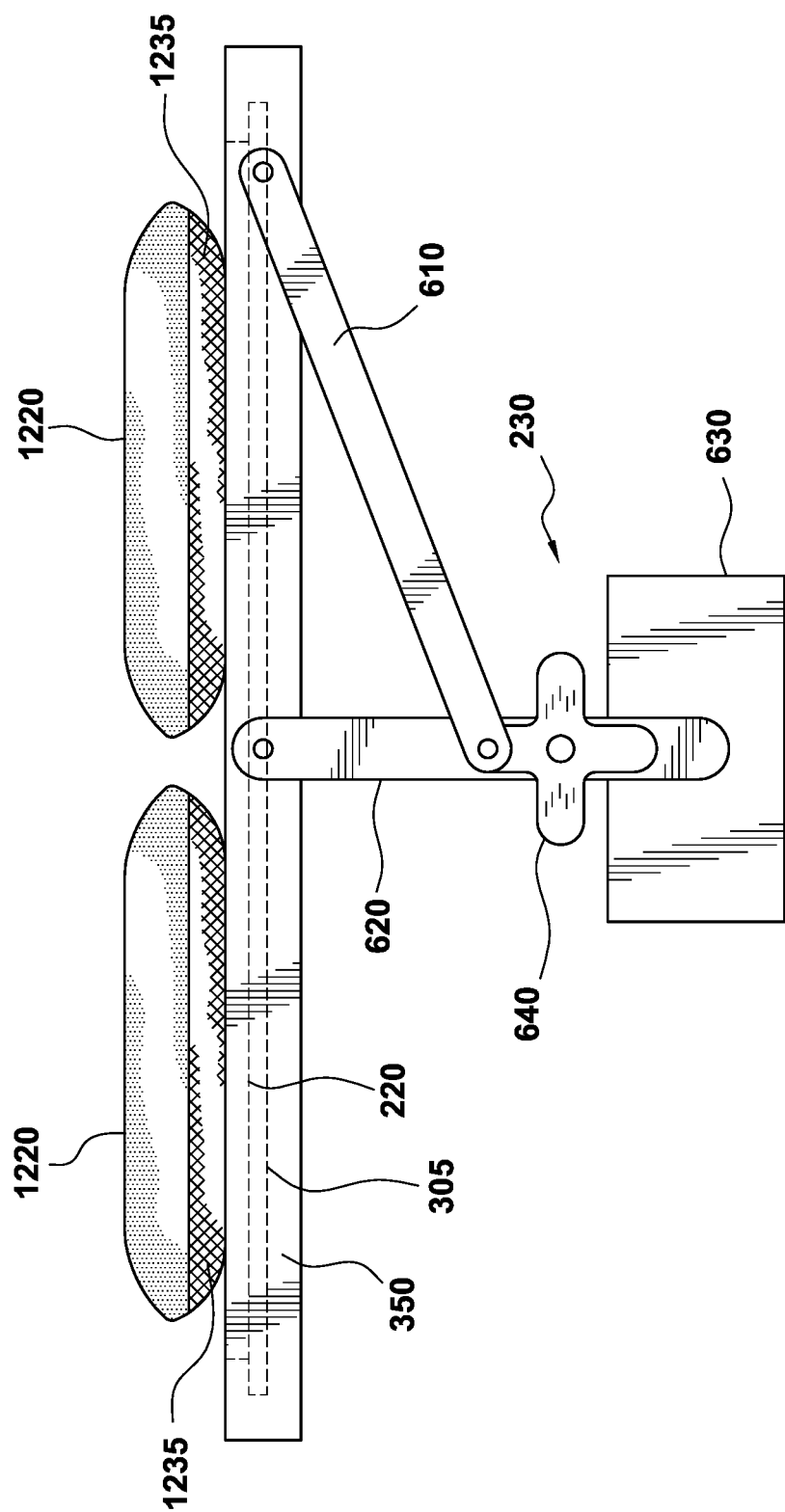
FIG. 12B shows the side view of a frame and tilt mechanism supporting multiple bags with cell culture in accordance with an embodiment.
Figure 12C:
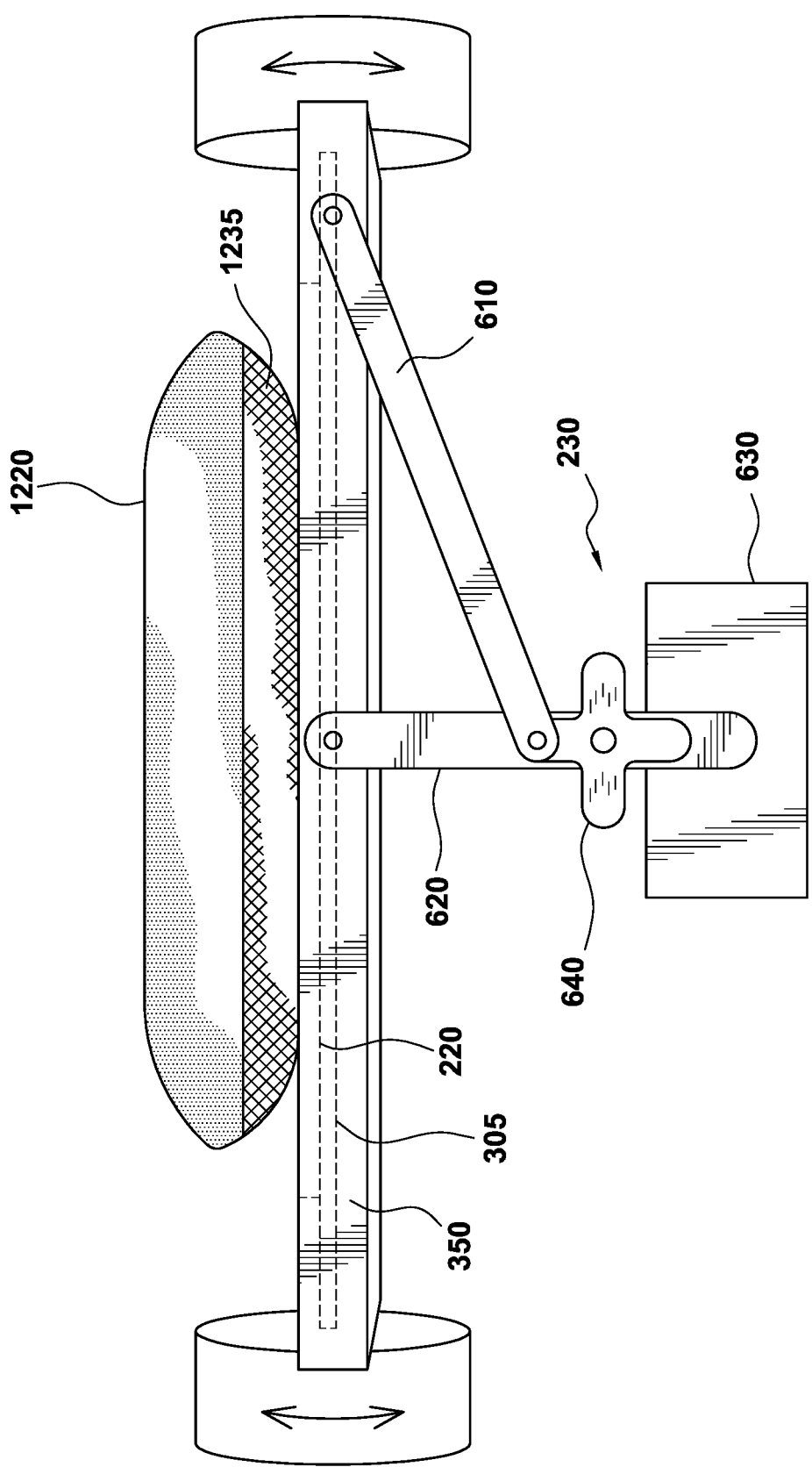
FIG. 12C shows a side view of the frame and tilt mechanism supporting a bag with cell culture in which the frame is equipped with tilting servos in accordance with an embodiment.

In another embodiment, a cell culture may be contained in a container disposed on tray 220. FIG. 12A shows a side view of frame 350 and tilt mechanism 230 in accordance with an embodiment. A bag 1220 containing a cell culture 1235 is disposed on tray 220. Although not shown, bag 1220 can be in fluid communication with the other components of the reactor system to optimize cell growth. Tray motion controller 290 may use methods similar to those described herein to control the motion of tray 220 in order to optimize the growth of cell culture 1235. While cell culture 1235 is depicted within bag 1220, cell culture 1235 can be disposed in any suitable container for cell growth such as a flask. As further shown in FIG. 12B, a plurality of bags 1220 can also be disposed on tray 220. Although not shown, the plurality of bags 1220 can also be in fluid communication with each other in addition to being in fluid communication with the other components of the reactor system to optimize cell growth. FIG. 12C shows a further embodiment in which frame 350 is equipped with tilting servos (not labelled) at opposite ends of frame 350 to facilitate access to cell culture 1235.

Various techniques may be used to generate a measure of cell density, determine a characteristic of a cell culture, or to process and/or analyze an image.

For example, U.S. Pat. No. 9,412,176, issued Aug. 9, 2016, which is incorporated by reference herein in its entirety, discloses methods, systems and articles of manufacture for processing and analyzing images. In particular, U.S. Pat. No. 9,412,176 discloses methods, systems and articles of manufacture for generating an edge-based feature descriptor for a digital image. Various embodiments can provide efficient image-based object recognition capabilities for texture-rich images as well as texture-poor images. In one embodiment, a plurality of edges are detected within a digital image. The digital image may be, for example, a video frame of a video stream or a rendered image. The plurality of edges may be detected based on one of tensor voting and a Canny edge detection algorithm. An anchor point located along an edge of the plurality of edges is selected. The anchor point may be a feature corresponding to at least one of a scale-invariant feature transform (SIFT), Fast Retina Keypoint (FREAK), Histograms of Oriented Gradient (HOG), Speeded Up Robust Features (SURF), DAISY, Binary Robust Invariant Scalable Keypoints (BRISK), FAST, Binary Robust Independent Elementary Features (BRIEF), Harris Corners, Edges, Gradient Location and Orientation Histogram (GLOH), Energy of image Gradient (EOG) or Transform Invariant Low-rank Textures (TILT) feature. An analysis grid associated with the anchor point is generated, the analysis grid including a plurality of cells. An analysis grid associated with the anchor point may have a geometric center at the anchor point, and may include one of a polar grid, a radial polar grid or a rectilinear grid. An anchor point normal vector comprising a normal vector of the edge at the anchor point is calculated. The anchor point normal vector may be one of a Harris matrix eigenvector or a geometric normal vector orthogonal to the edge at a pixel coordinate of the anchor point. One or more edge pixel normal vectors comprising normal vectors of the edge at one or more locations along the edge within the cells of the analysis grid are calculated. The edge pixel normal vectors may be one of a Harris matrix eigenvector or a geometric normal vector orthogonal to the edge at a pixel coordinate. A histogram of similarity is generated for each of one or more cells of the analysis grid, each histogram of similarity being based on a similarity measure between each of the edge pixel normal vectors within a cell and the anchor point normal vector, and a descriptor is generated for the analysis grid based on the histograms of similarity. Generating the descriptor may include concatenating data from the histograms of similarity for one or more of the cells of the analysis grid. An image-based object recognition search may be facilitated using the descriptor for the analysis grid.

For example, U.S. Pat. No. 9,466,009, issued Oct. 11, 2016, which is incorporated by reference herein in its entirety, discloses apparatus, systems and methods for processing and analyzing images. In particular, U.S. Pat. No. 9,466,009 discloses apparatus, systems and methods for processing and analyzing images in which an object data processing system can, in real-time, determine which recognition algorithms should be applied to regions of interest in a digital representation. In one embodiment, a system comprises a plurality of diverse recognition modules and a data preprocessing module. Each module represents hardware configured to execute one or more sets of software instructions stored in a non-transitory, computer readable memory. For example, the recognition modules can comprise at least one recognition algorithms (e.g., SIFT, DAISY, ASR, OCR, etc.). Further, the data preprocessing module can be configured, via its software instructions, to obtain a digital representation of a scene. The digital representation can include one or more modalities of data including image data, video data, sensor data, news data, biometric data, or other types of data. The preprocessing module leverages an invariant feature identification algorithm, preferably one that operates quickly on the target data, to generate a set of invariant features from the digital representation. One suitable invariant identification feature algorithm that can be applied to image data includes the FAST corner detection algorithm. The preprocessing module further clusters or otherwise groups the set of invariant features into regions of interest where each region of interest can have an associated region feature density (e.g., features per unit area, feature per unit volume, feature distribution, etc.). The preprocessor can then assign each region one or more of the recognition modules as a function of the region's feature density. Each recognition module can then be configured to process their respective regions of interest according the recognition module's recognition algorithm.

For example, U.S. Pat. No. 9,501,498, issued Nov. 22, 2016, which is incorporated by reference herein in its entirety, discloses apparatus, systems and methods in which real-world objects can be ingested into an object recognition database using canonical shapes. In one embodiment, an object recognition ingestion system has a canonical shape database and an object ingestion engine. The canonical shape database is programmed to perform the step of storing one or more shape objects where the shape objects represent manageable data objects. Each shape object can be considered to represent a known canonical shape or object template; for example a sphere, cylinder, pyramid, mug, vehicle, or other type of shape. Further the shape objects include geometrical attributes reflecting the aspects of their corresponding shape, a radius, length, width, or other geometrical features for example. Of particular note, the shape objects also include one or more reference point-of-views (PoVs) that indicate preferred perspectives from which an object having a corresponding shape could be analyzed. The object ingestion engine can be coupled with the canonical shape database and programmed to perform the step of fulfilling the roles or responsibilities of ingesting object information to populate an object recognition database. The engine obtains image data that includes a digital representation of a target object of interest. The engine further derives one or more edges of the object from the image data, possibly by executing an implementation of one or more edge detection algorithms. Each of the derived edges includes geometrical information relating to the nature of the edge (e.g., radius, length, edgels, edgelets, edge descriptors, etc.). The engine can use the information relating to the set of edges to obtain a set of shape objects as a result set from the canonical shape database. In some embodiments, the edge geometrical information is used to identify shape objects that have compatible or complementary shape attributes as the set of edges. At least one of the shape objects in the result set is selected as a candidate shape object for building an object model of the target object. Thus, the engine can continue analyzing the target object by generating one or more object models of the target object based on the selected shape and the image data. For example, the geometrical attributes of the shape can be adjusted or take on specific values related to the object, and the image data of the object can be used to texture and/or paint the object model. Further, the engine is programmed to perform the step of using the selected shape's reference PoVs to determine from which PoVs the object model should be analyzed to generate key frame information. The engine uses the reference PoVs to drive a set of model key frame PoVs, possibly based on one or more rules or object symmetry, which will be used for generating the key frames. Further, the engine instantiates a descriptor object model from the object model where the descriptor model includes recognition algorithm descriptors (e.g., SIFT, FREAK, FAST, etc.) having locations within or on the object model and relative to the model key frame PoVs. From the descriptor object model, the engine further compiles one or more key frame bundles that can be used by other devices to recognize the target object. The key frame bundles can include one or more of an image of the object model from a corresponding key frame PoV, a descriptor related to the key frame PoV, a normal vector, or other recognition information. The key frame bundles can be stored in an object recognition database for consumption by other devices when they are required to recognize the target object. Further the key frame bundles can be correlated with object information, address, content information, applications, software, commands, or there types of media as desired.

For example, U.S. Pat. No. 9,558,426, issued Jan. 31, 2017, which is incorporated by reference herein in its entirety, discloses methods, systems and articles of manufacture for identifying robust features within a training image. Various embodiments can allow for building compact and efficient recognition libraries for image-based object recognition. In one embodiment, robust features are identified within a training image. The training image may be an undistorted image, an infrared-filtered image, an x-ray image, a 360-degree view image, a machine-view image, a frame of video data, a graphical rendering or a perspective-view of a three-dimensional object, and may be obtained by capturing a video frame of a video stream via an image capture device. Training features are generated by applying a feature detection algorithm to the training image, each training feature having a training feature location within the training image. At least a portion of the training image is transformed into a transformed image in accordance with a predefined image transformation. A plurality of image transformations may be presented to a user for selection as the predefined image transformation, and the predefined image transformation may be selected independently from a method used to capture the training image. Transform features are generated by applying the feature detection algorithm to the transformed image, each transform feature having a transform feature location within the transformed image. The training feature locations of the training features are mapped to corresponding training feature transformed locations within the transformed image in accordance with the predefined image transformation, and a robust feature set is compiled by selecting robust features, wherein each robust feature represents a training feature having a training feature transformed location proximal to a transform feature location of one of the transform features. Each of the training features and transform features may be described by a feature descriptor in accordance with the feature detection algorithm. Each of the training feature locations may comprise a pixel coordinate, and each of the transform feature locations may comprise a transformed pixel coordinate. The feature detection algorithm may include at least one of a scale-invariant feature transform (SIFT), Fast Retina Keypoint (FREAK), Histograms of Oriented Gradient (HOG), Speeded Up Robust Features (SURF), DAISY, Binary Robust Invariant Scalable Keypoints (BRISK), FAST, Binary Robust Independent Elementary Features (BRIEF), Harris Corners, Edges, Gradient Location and Orientation Histogram (GLOH), Energy of image Gradient (EOG) or Transform Invariant Low-rank Textures (TILT) feature detection algorithm.

For example, U.S. Pat. No. 9,633,042, issued Apr. 25, 2017, which is incorporated by reference herein in its entirety, discloses apparatuses, systems and methods in which one or more computing devices discover scene attributes that help enhance feature-based object recognition. In some embodiments, features are derived from a digital representation of an image captured by an image sensor and traits are derived from scene trait sensor data, a particular set of scene trait sensor data being related to a particular digital representation by the time and scene at which the data was captured. In some embodiments, an object recognition trait identification system includes a trait analysis engine. In some embodiments, the system also includes a scene trait database. In some embodiments, the system also includes an object recognition system and corresponding object recognition database. The scene trait database is configured or programmed to store one or more scene traits that represent the properties of a scene or environment (e.g., lighting conditions, wireless field strengths, gravity, etc.). Each of the scene traits can have corresponding values (e.g., scalar, vector, etc.) within a scene attribute space. The trait analysis engine leverages the scene traits in an attempt to differentiate among similar object recognition features that are commonly associated with an object or with many objects. The trait analysis engine is configured to obtain a digital representation (e.g., images, video, sound, etc.) of an object in a scene and then apply one or more recognition algorithms to the digital representation to derive one or more features, where the features exist within a feature space. The engine further compiles a portion of the features into at least one similarity feature set, where the features within the similarity feature set are considered similar to each other according to a similarity measure (e.g., low variance, close proximity in the feature space, clustering, etc.). Although the features within the similarity feature set are considered similar to each other within the feature space, the engine analyzes the similar features with respect to one or more scene traits in the non-feature, scene attribute space thereby generating one or more trait variances with respect to known scene traits. The trait variances provide the engine sufficient information to select at least one trait as a distinguishing trait for the features in the similarity feature set. The features can then be stored in the object recognition database along with the distinguishing trait information. In alternative embodiments, scene trait analysis is applied to recognition of all objects across a plurality of scene captures, whether or not those objects are associated with descriptors in a similarity feature set.

For example, U.S. Pat. No. 9,659,033, issued May 23, 2017, which is incorporated by reference herein in its entirety, discloses an apparatus comprising a memory communicatively coupled to a processor that can be configured to operate as an object recognition platform. The memory can store one or more object-specific metric maps, which map an image color space of target object image data to a set of metric values selected to enhance detection of descriptors with respect to a specific object and with respect to a target algorithm. For example, an object-specific metric map can map an RGB value from each pixel of a digital representation of a target object to single metric channel of recognition values that can be processed by an image processing algorithm executing on the processor. The processor, when operating as a recognition engine, can execute various object recognition steps, including for example, obtaining one or more target object-specific metric maps from the memory, obtaining a digital representation of a scene and including image data (e.g., via a sensor of a device storing the memory and processor, etc.), generating altered image data using an object-specific metric map, deriving a descriptor set using an image analysis algorithm, and retrieving digital content associated with a target object as a function of the metric-based descriptor set.

For example, U.S. Pat. No. 9,665,606, issued May 30, 2017, which is incorporated by reference herein in its entirety, discloses apparatus, systems and methods in which one or more computing devices can operate as image processing systems to identify edges representing in image data and use the identified edges to recognizing objects or classify objects in a manner that reduces false positives. For example, a method of enabling a device or a system to take an action based on image data is disclosed. The method includes obtaining image data having a digital representation of an object of interest. An image recognition system, which is preferably executed by an image processing device (e.g., a tablet, smart phone, kiosk, augmented or virtual reality glasses, etc.) is programmed to perform such method. The method further comprises analyzing the image data to generate a collection of edges. For example, the method can include generating a collection of edges by executing an implementation of a co-circularity algorithm on at least a portion of the image data related to the object. In more embodiments, edges in the collection can include a perception measure (e.g., saliency, smoothness, length, etc.) indicating an "edged-nes s" associated with the edge from a perception perspective. From the collection of edges, the image recognition system can select a set of candidate edges based in part on the perception measure. These candidate set of edges represents possible starting points from which the image processing device can construct edge-based descriptors. Thus, the method can construct pixel level edgelets from the image data for the edges in the candidate set. The method then derives a plurality of edge-based descriptors from the edgelets where the descriptors represent constellations of edgelets. Once the constellations, or their corresponding descriptors, are identifying, they can be used to configure a device or the image recognition system to take an action based on one or more of the descriptors in the plurality of edge-based descriptors. For example, the action can include indexing content related to the object in a content database (e.g., database, file system, spill tree, k-d tree, etc.) according the associated edge-based descriptors so that the content can be later retrieved. Another example action includes using the edge-based descriptors to query the content database for content related to the object.

Figure 14:
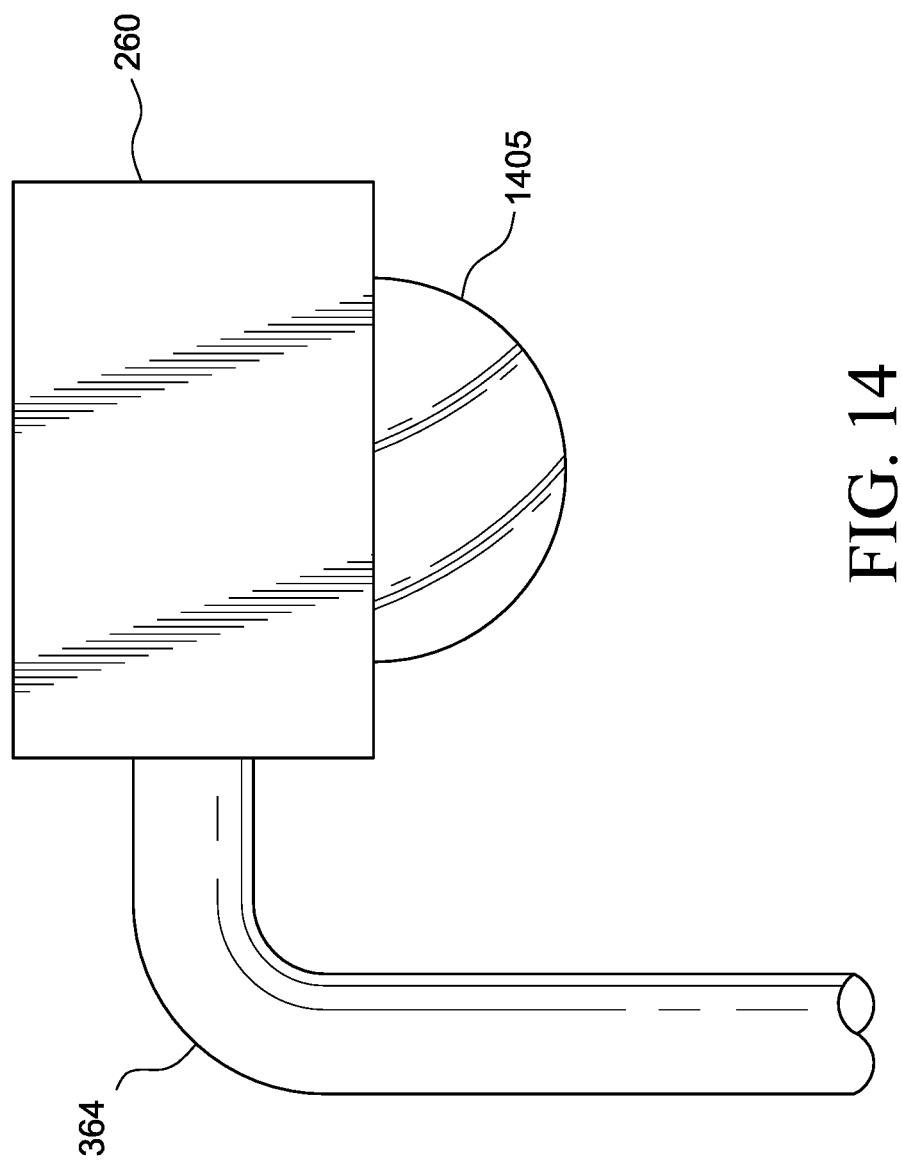
FIG. 14 shows a camera supported by an arm in accordance with an embodiment.

In another embodiment illustrated in FIG. 14, a camera having a fisheye lens may be used to obtain wider or panoramic images. FIG. 14 shows camera 260 supported by arm 364 in accordance with an embodiment. Camera 260 includes a fisheye lens 1405. Fisheye lens 1405 enables camera 260 to obtain a wide and/or panoramic view of any culture located on tray 220.

Figure 15B:
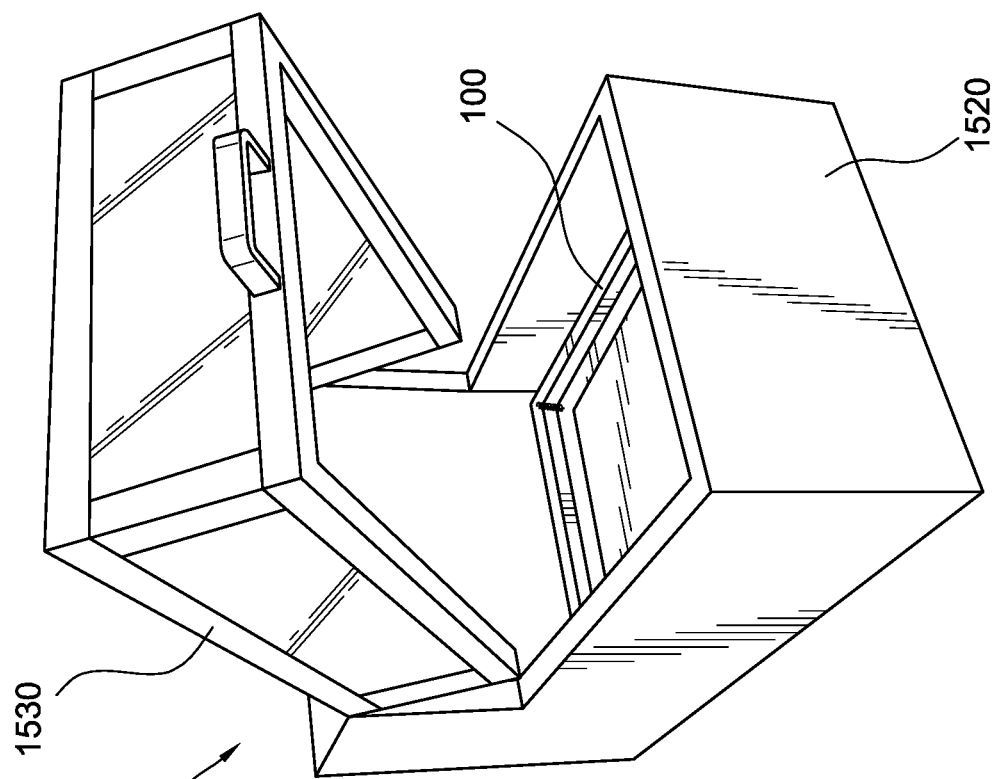
FIGS. 15A-15B show components of a bioreactor system in accordance with an embodiment.
Figure 15A:
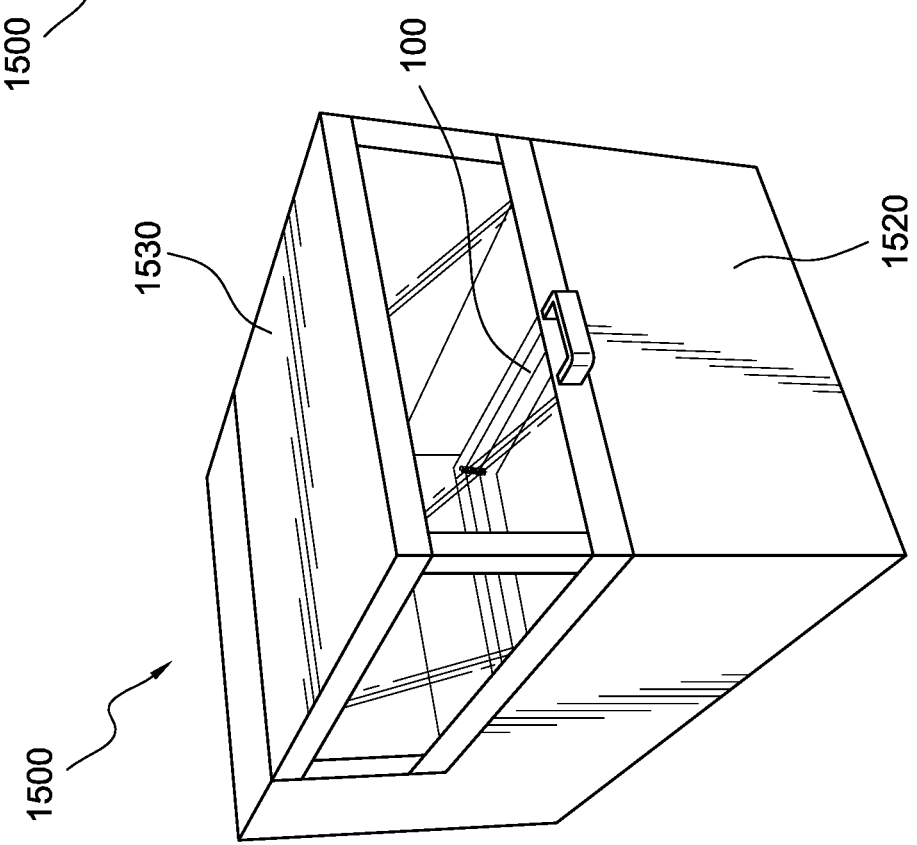

In another embodiment, a cell control system, such as cell culture system 100, including a tray control system similar to tray control system 110 and a computer such as computer 120, are disposed within a bioreactor system. FIGS. 15A-15B show components of a bioreactor system 1500 in accordance with an embodiment. Bioreactor system 1500 includes a compartment 1520 and a door 1530. Cell culture system 100 is disposed inside compartment 1520. Door 1530 has a closed position, as shown in FIG. 15A, and an open position, as shown in FIG. 15B. Door 1530 may be opened to allow access to cell culture system 1530, for example. Cell culture system 100 may be configured and/or modified to fit and operate within compartment 1520.

In various embodiments, the method steps described herein, including the method steps described in FIGS. 11A and 11B, may be performed in an order different from the particular order described or shown. In other embodiments, other steps may be provided, or steps may be eliminated, from the described methods.

Systems, apparatus, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be used within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc.

Systems, apparatus, and methods described herein may be implemented using a computer program product tangibly embodied in an information carrier, e.g., in a non-transitory machine-readable storage device, for execution by a programmable processor; and the method steps described herein, including one or more of the steps of FIGS. 11A and 11B, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 13:
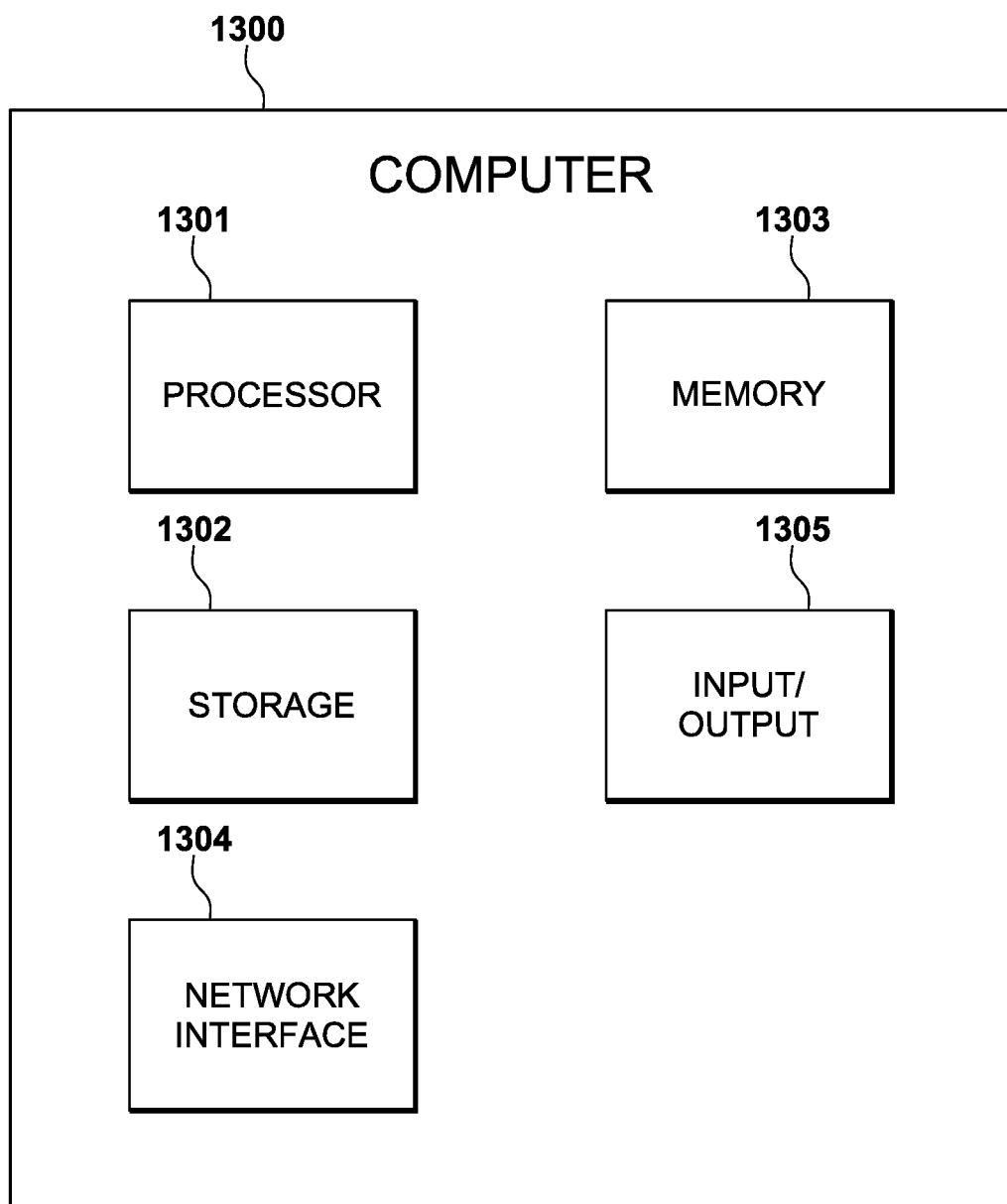
FIG. 13 shows components of an exemplary computer that may be used to implement certain embodiments.

A high-level block diagram of an exemplary computer that may be used to implement systems, apparatus and methods described herein is illustrated in FIG. 13. Computer 1300 includes a processor 1301 operatively coupled to a data storage device 1302 and a memory 1303. Processor 1301 controls the overall operation of computer 1300 by executing computer program instructions that define such operations. The computer program instructions may be stored in data storage device 1302, or other computer readable medium, and loaded into memory 1303 when execution of the computer program instructions is desired. Thus, the method steps of FIGS. 11A and 11B can be defined by the computer program instructions stored in memory 1303 and/or data storage device 1302 and controlled by the processor 1301 executing the computer program instructions. For example, the computer program instructions can be implemented as computer executable code programmed by one skilled in the art to perform an algorithm defined by the method steps of FIGS. 11A and 11B. Accordingly, by executing the computer program instructions, the processor 1301 executes an algorithm defined by the method steps of FIGS. 11A and 11B. Computer 1300 also includes one or more network interfaces 1304 for communicating with other devices via a network. Computer 1300 also includes one or more input/output devices 1305 that enable user interaction with computer 1300 (e.g., display, keyboard, mouse, speakers, buttons, etc.).

Processor 1301 may include both general and special purpose microprocessors, and may be the sole processor or one of multiple processors of computer 1300. Processor 1301 may include one or more central processing units (CPUs), for example. Processor 1301, data storage device 1302, and/or memory 1303 may include, be supplemented by, or incorporated in, one or more application-specific integrated circuits (ASICs) and/or one or more field programmable gate arrays (FPGAs).

Data storage device 1302 and memory 1303 each include a tangible non-transitory computer readable storage medium. Data storage device 1302, and memory 1303, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 1305 may include peripherals, such as a printer, scanner, display screen, etc. For example, input/output devices 1305 may include a display device such as a cathode ray tube (CRT) or liquid crystal display (LCD) monitor for displaying information to the user, a keyboard, and a pointing device such as a mouse or a trackball by which the user can provide input to computer 1300.

One skilled in the art will recognize that an implementation of an actual computer or computer system may have other structures and may contain other components as well, and that FIG. 13 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:
1. A method comprising:
providing a cell culture in need of cell growth optimization, the cell culture being provided in a cell culture container configured to grow cells;
generating an image of the cell culture;
determining a characteristic of the cell culture to facilitate cell growth optimization based on the image, wherein the characteristic is selected from the group consisting of cell density, cell growth patterns, and cell morphology; and adjusting at least one a motion selected from the group consisting of tilting and shaking of the cell culture container based on the characteristic to facilitate cell growth optimization.

2. The method of claim 1, further comprising:
receiving, from a sensor, motion data indicating a motion of the cell culture container;
determining a first movement of the cell culture container based on the motion data;
adjusting the motion of the cell culture container by determining a second movement of the cell culture container based on the characteristic, the second movement being different from the first movement.

3. The method of claim 1, further comprising:
using a camera to capture the image of the cell culture; and
analyzing the image data to determine the measure of cell density.

4. The method of claim 1, wherein the measure of cell density comprises a second measure of average cell density.

5. The method of claim 1, wherein determining the measure of cell density comprises determining a count of cell clusters.

6. The method of claim 1, further comprising:
determining whether the measure of cell density exceeds a predetermined limit; and
adjusting a movement of the cell culture in response to determining that the measure of cell density exceeds the predetermined limit.

7. The method of claim 1, wherein determining the measure of cell density comprises:
identifying one or more cell morphologies among cells in the cell culture; and
determining one or more second measures of cell densities based on the one or more cell morphologies.

8. The method of claim 1, wherein the cell culture container is disposed on a tray configured to receive the cell culture container and configured to tilt or shake the cell culture container.

9. The method of claim 8, wherein:
adjusting the tilting motion of the cell culture container includes causing the cell culture container on the tray to tilt back and forth at one of a lower rate and a higher rate;
adjusting the shaking motion of the cell culture container on the tray to shake back and forth at one of a lower rate and a higher rate; or
adjusting both the tilting motion and shaking motion of the cell culture container.

10. An apparatus comprising:
a first device configured to:
hold a cell culture container containing a cell culture in need of cell growth optimization, the cell culture container being configured to grow cells; and
cause a movement of the cell culture container;
a second device configured to generate an image of the cell culture; and
at least one processor configured to:
determine a characteristic of the cell culture to facilitate cell growth optimization based on the image, wherein the characteristic is selected from the group consisting of cell density, cell growth patterns, and cell morphology; and
cause the first device to adjust at least one motion selected from the group consisting of tilting and shaking of the cell culture container based on the characteristic to facilitate cell growth optimization.

11. The apparatus of claim 10, wherein the processor is further configured to:
determine a measure of average cell density based on the image.

12. The apparatus of claim 10, wherein the processor is further configured to:
determine a count of cell clusters based on the image;
determine the measure of cell density based on the count of cell clusters; or
determine both the count of cell clusters and the measure of cell density.

13. A system comprising:
a tray configured to hold a cell culture container containing a cell culture in need of cell growth optimization, the cell culture container being configured to grow cells;
a camera configured to capture an image of the cell culture;
a device configured to control a movement of the tray; and
a processor configured to:
determine a first movement of the tray;
receive from the camera data representing an image of the cell culture;
determine a characteristic of the cell culture to facilitate cell growth optimization based on the image data, wherein the characteristic is selected from the group consisting of cell density, cell growth patterns, and cell morphology;
determine a second movement of the tray based on the characteristic, the second movement being different from the first movement; and
cause the device to cause the tray to move in accordance with the second movement to facilitate cell growth optimization, wherein the first movement and the second movement are selected from the group consisting of tilting and shaking.

14. The system of claim 13, further comprising:
a sensor configured to obtain motion data indicating a motion of the tray,
wherein the processor is further configured to:
receive the motion data from the sensor; and
determine the first movement of the tray based on the motion data.

15. The system of claim 13, wherein the processor is further configured to:
determine a second measure of average cell density based on the image data.

16. The system of claim 15, wherein the processor is further configured to:
determine a count of cell clusters;
determine the measure of cell density based on the count of cell clusters; or
determine both the count of cell clusters and the measure of cell density.

17. The system of claim 13, wherein the processor is further configured to:
determine that the measure of cell density exceeds a predetermined limit;
determine the second movement in response to the determination that that the measure of cell density exceeds the predetermined limit; or
determine both the measure of cell density exceeds a predetermined limit and the second movement.

18. The system of claim 13, wherein the processor is further configured to:
  adjust at least one motion selected from the group consisting of tilting and shaking of the tray to determine the second movement of the tray.

19. The system of claim 18, wherein the processor is further configured to perform one of the following:
  cause the tray to tilt back and forth at one of a lower rate and a higher rate;
  cause the tray to shake back and forth at one of a lower rate and a higher rate; or
  cause the tray to both tilt back and forth and shake back and forth.

* * * * *